US010689324B2

(12) United States Patent
Farr et al.

(10) Patent No.: US 10,689,324 B2
(45) Date of Patent: Jun. 23, 2020

(54) METABOLISM RESISTANT FENFLURAMINE ANALOGS AND METHODS OF USING THE SAME

(71) Applicant: ZOGENIX INTERNATIONAL LIMITED, Berkshire (GB)

(72) Inventors: Stephan J. Farr, Orinda (CA); Brooks M. Boyd, Berkeley, CA (US)

(73) Assignee: ZOGENIX INTERNATIONAL LIMITED, Berkshire, OT (GB)

(*) Notice: Subject to any disclaimer, the term of this patent is extended or adjusted under 35 U.S.C. 154(b) by 0 days.

(21) Appl. No.: 16/064,377

(22) PCT Filed: Dec. 20, 2016

(86) PCT No.: PCT/US2016/067852
§ 371 (c)(1),
(2) Date: Jun. 20, 2018

(87) PCT Pub. No.: WO2017/112701
PCT Pub. Date: Jun. 29, 2017

(65) Prior Publication Data
US 2019/0002391 A1 Jan. 3, 2019

Related U.S. Application Data

(60) Provisional application No. 62/271,168, filed on Dec. 22, 2015.

(51) Int. Cl.
C07C 211/29 (2006.01)
A61K 31/137 (2006.01)
A61K 45/06 (2006.01)
C07D 211/22 (2006.01)
C07C 215/64 (2006.01)
C07D 221/18 (2006.01)
C07D 207/08 (2006.01)
A61P 25/08 (2006.01)

(52) U.S. Cl.
CPC .......... C07C 211/29 (2013.01); A61K 31/137 (2013.01); A61K 45/06 (2013.01); A61P 25/08 (2018.01); C07C 215/64 (2013.01); C07D 207/08 (2013.01); C07D 211/22 (2013.01); C07D 221/18 (2013.01); C07C 2601/04 (2017.05); C07C 2601/14 (2017.05)

(58) Field of Classification Search
CPC ................................ A61P 25/08; C07C 211/29
See application file for complete search history.

(56) References Cited

U.S. PATENT DOCUMENTS

| 3,117,160 | A | 1/1964 | Holland |
| 3,198,833 | A | 8/1965 | Beregi |
| 3,759,979 | A | 9/1973 | Beregi et al. |
| 4,824,987 | A | 4/1989 | Kleeman |
| 5,587,398 | A | 12/1996 | Elmaleh et al. |
| 5,808,156 | A | 9/1998 | Cannata et al. |
| 5,811,586 | A | 9/1998 | Cannata et al. |
| 6,045,501 | A | 4/2000 | Elsayed et al. |
| 6,315,720 | B1 | 11/2001 | Williams et al. |
| 6,561,976 | B2 | 5/2003 | Elsayed et al. |
| 6,561,977 | B2 | 5/2003 | Williams et al. |
| 6,755,784 | B2 | 6/2004 | Williams et al. |
| 6,869,399 | B2 | 3/2005 | Williams et al. |
| 6,908,432 | B2 | 6/2005 | Elsayed et al. |
| 7,141,018 | B2 | 11/2006 | Williams et al. |
| 7,585,493 | B2 | 9/2009 | Hale |
| 7,668,730 | B2 | 2/2010 | Reardan et al. |
| 7,765,106 | B2 | 7/2010 | Reardan et al. |
| 7,765,107 | B2 | 7/2010 | Reardan et al. |
| 7,797,171 | B2 | 9/2010 | Reardan et al. |
| 7,874,984 | B2 | 1/2011 | Elsayed et al. |
| 7,895,059 | B2 | 2/2011 | Reardan et al. |
| 7,959,566 | B2 | 6/2011 | Williams et al. |
| 8,204,763 | B2 | 6/2012 | Elsayed et al. |
| 8,263,650 | B2 | 9/2012 | Cook et al. |
| 8,315,886 | B2 | 11/2012 | Williams et al. |
| 8,386,274 | B1 | 2/2013 | Pinsonneault |
| 8,457,988 | B1 | 6/2013 | Reardan et al. |
| 8,589,182 | B1 | 11/2013 | Reardan et al. |
| 8,589,188 | B2 | 11/2013 | Elsayed et al. |
| 8,626,531 | B2 | 1/2014 | Williams et al. |
| 8,731,963 | B1 | 5/2014 | Reardan et al. |

(Continued)

FOREIGN PATENT DOCUMENTS

EP 0 441 160 8/1991
EP 2 399 513 12/2011

(Continued)

OTHER PUBLICATIONS

Coma et al (2013), STN International (Columbus, Ohio) HCAPLUS database, Accession No. 2013: 682383.*
Dimpfel et al (2006), STN International (Columbus, Ohio), HCAPLUS database, Accession No. 2006: 1205690.*
Bird et al (2013), STN International (Columbus, Ohio), HCAPLUS database, Accession No. 2013: 83254.*
Aicardi et al., "Treatment of Self-Induced Photosensitive Epilepsy with Fenfluramine" New England Journal of Medicine (1985) 313:1419.
Aicardi et al., "Syncopal Attacks Compulsively Self-induced by Valsalva's Maneuver Associated with Typical Absence Seizures" Archives of Neurology (1988) 45:923-925.
Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

(Continued)

Primary Examiner — Golam M Shameem
(74) Attorney, Agent, or Firm — Karl Bozicevic; Bozicevic Field & Francis LLP

(57) ABSTRACT

Metabolism-resistant fenfluramine analogs are provided. The subject fenfluramine analogs find use in the treatment of a variety of diseases. For example, methods of treating epilepsy by administering a fenfluramine analog to a subject in need thereof are provided. Also provided are methods of suppressing appetite in a subject in need thereof. Pharmaceutical compositions for use in practicing the subject methods are also provided.

3 Claims, No Drawings

(56) References Cited

U.S. PATENT DOCUMENTS

| | | |
|---|---|---|
| 10,351,509 B2 | 7/2019 | Londesbrough |
| 10,351,510 B2 | 7/2019 | Londesbrough |
| 2002/0038310 A1 | 3/2002 | Reitberg |
| 2003/0007934 A1 | 1/2003 | Rabinowitz et al. |
| 2004/0249212 A1 | 12/2004 | Smallridge et al. |
| 2008/0004904 A1 | 1/2008 | Tran |
| 2009/0171697 A1 | 7/2009 | Glauser |
| 2010/0088778 A1 | 4/2010 | Mulley |
| 2012/0065999 A1 | 3/2012 | Takatoku |
| 2013/0218586 A1 | 8/2013 | Huser |
| 2014/0142140 A1 | 5/2014 | Bird |
| 2014/0348966 A1 | 11/2014 | Balemba |

FOREIGN PATENT DOCUMENTS

| | | |
|---|---|---|
| EP | 3170807 | 5/2017 |
| RU | 2317104 | 2/2008 |
| RU | 103209 | 3/2011 |
| WO | WO 01/86506 | 11/2001 |
| WO | WO 2003/026591 | 4/2003 |
| WO | WO 2007/073503 | 6/2007 |
| WO | WO 2010/104841 | 9/2010 |
| WO | WO 03/077847 | 9/2013 |
| WO | WO 2014/177676 | 11/2014 |

OTHER PUBLICATIONS

Arzimanoglou, Alexis, "Dravet syndrome: From electroclinical characteristics to molecular biology" Epilepsia (2009) 50(Suppl 8):3-9.

Boel and Casaer et al., "Add-on Therapy of Fenfluramine in Intractable Self-Induced Epilepsy" Neuropaediatrics (1996) 27(4):171-173.

Boel and Casaer et al., "Fenfluramine as a Potential Antiepileptic Drug" Epilepsia (2002) 43(2):205-206.

Brunklaus et al., "Prognostic, clinical and demographic features in SCN1A mutation-positive Dravet syndrome" BRAIN (2012) p. 1-8.

Ceulemans, "Overall management of patients with Dravet syndrome" Developmental Medicine & Child Neurology (2011) 53:19-23.

Ceulemans et al., "Successful use of fenfluramine as an add-on treatment for Dravet syndrome" Epilepsia (2012) 53(7):1131-1139.

Ceulemans B. et al., "Successful use of Fenflurarmine as add-on treatment in Dravet syndrome: a two year prospective follow up", European Journal of Paediatric Neurology (Sep. 1, 2013) vol. 17:01101866.

Chiron et. al., "The pharmacologic treatment of Dravet syndrome" Epilepsia (2011) 52(Suppl 2):72-75.

Clemens, Bela, "Dopamine agonist treatment of self-induced pattern-sensitive epilepsy. A case report" Epilepsy Research (1988) 2:340-343.

Cozzi et al., "Indan Analogs of Fenfluramine and Norfenfluramine Have Reduced Neurtoxic Potential" Pharmacology Biochemistry and Behavior (1998) 59(3):709-715.

Gentsch et al., "Laboratory Research Fenfluramine Blocks Low-Mg2'-Induced Epileptiform Activity in Rat Entorhinal Cortex" Epilepsia (Jan. 1, 2000), pp. 925-928.

Gross et al., "The influence of the sparteine/debrisoquine genetic polymorphism on the disposition of dexfenfluramine" Br J Clin Pharmacol (1996) 41:311-317.

Lambert et al., "Inductive Enhancement of Aryl Participation" Journal of the American Chemical Society (Apr. 27, 1977) 99(9):3059-67.

Meador K J., "Seizure reduction with fluoxetin in an adult woman with Dravet syndrome", Epilepsy & Behavior Case Reports, Elsevier BV, NL (Jan. 1, 2014) 2(1):54-56.

Mulley et al., "SCN1A Mutations and Epilepsy" Human Mutation (2005) 25:535-542.

Patani et al;, "Bioisosterism: A Rational Approach to Drug Design" Chem. Rev. (1996) 96:3147-3176.

Remington, "The Science and Practice of Pharmacy", Nineteenth Edition (1995), pp. 710-712.

Rothman et al., "(+)-Fenfluramine and Its Major Metabolite, (+)-Norfenfluramine, Are Potent Substrates for Norepinephrine Transporters" The Journal of Pharmacology and Experimental Therapeutics (2003) 305(3)1191-1199.

Tran et al., "Dakin-West Synthesis of β-Aryl Ketones" J. Org. Chem. (2006) 71:6640-6642.

Anonymous, "Determination That PONDIMIN (Fenfluramine Hydrochloride) Tablets, 20 Milligrams and 60 Milligrams, and PONDEREX (Fenfluramine Hydrychloride) Capsules, 20 Milligrams Were Withdrawn From Sale for Reasons of Safety or Effectiveness" Federal Register (Sep. 29, 2015) pp. 58490-58491.

Kaiser et al., "Synthesis and Anorectic Activity o Some 1-Benzylcyclopropylamines" Journal of Medicinal Chemistry, American Chemical Society, US (1970) 13(5):820-826.

\* cited by examiner

METABOLISM RESISTANT FENFLURAMINE ANALOGS AND METHODS OF USING THE SAME

CROSS-REFERENCE TO RELATED APPLICATIONS

Pursuant to 35 U.S.C. § 119 (e), this application claims the benefit of priority to U.S. Provisional Patent Application Ser. No. 62/271,168, filed Dec. 22, 2015, the disclosure of which application is hereby incorporated by reference herein in its entirety.

FIELD

This invention relates generally to the field of compounds structurally related to the amphetamine drug fenfluramine and their use in the treatment of neurological related diseases.

INTRODUCTION

Fenfluramine is an amphetamine drug that was once widely prescribed as an appetite suppressant to treat obesity. Fenfluramine is devoid of the psychomotor stimulant and abuse potential of D-amphetamine and interacts with the 5-hydroxytryptamine (serotonin, 5-HT) transporters to release 5-HT from neurons. Fenfluramine has been investigated for anticonvulsive activity in the treatment of Dravet Syndrome, or severe myoclonic epilepsy in infancy, a rare and malignant epileptic syndrome. This type of epilepsy has an early onset in previously healthy children.

Anorectic treatment with fenfluramine has been associated with the development of cardiac valvulopathy and pulmonary hypertension, including the condition cardiac fibrosis which led to the withdrawal of fenfluramine from world-wide markets. Interaction of fenfluramine's major metabolite norfenfluramine with the 5-HT2B receptor is associated with heart valve hypertrophy. In the treatment of epilepsy, the known cardiovascular risks of fenfluramine are weighed against beneficial anticonvulsive activity.

SUMMARY

Metabolism-resistant fenfluramine analogs are provided. The subject fenfluramine analogs find use in the treatment of a variety of diseases. For example, methods of treating epilepsy by administering a fenfluramine analog to a subject in need thereof are provided. Also provided are methods of suppressing appetite in a subject in need thereof. Pharmaceutical compositions for use in practicing the subject methods are also provided.

These and other objects, advantages, and features of the invention will become apparent to those persons skilled in the art upon reading the details of the metabolism-resistant fenfluramine analogs and methods of using the same as more fully described below.

Definitions

As used herein, the term "subject" refers to a mammal. Exemplary mammals include, but are not limited to, humans, domestic animals (e.g., a dog, cat, or the like), farm animals (e.g., a cow, a sheep, a pig, a horse, or the like) or laboratory animals (e.g., a monkey, a rat, a mouse, a rabbit, a guinea pig, or the like). In certain embodiments, the subject is human "Patient" refers to human and non-human subjects, especially mammalian subjects.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein, the term pKa refers to the negative logarithm (p) of the acid dissociation constant (Ka) of an acid, and is equal to the pH value at which equal concentrations of the acid and its conjugate base form are present in solution.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$-).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-aryl, —SO$_2$— heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO— alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, $-NR^{80}R^{80}$ is meant to include $-NH_2$, $-NH$-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, $-R^{60}$, halo, $-O^-M^+$, $-OR^{70}$, $-SR^{70}$, $-S^-M^+$, $-NR^{80}R^{80}$, trihalomethyl, $-CF_3$, $-CN$, $-OCN$, $-SCN$, $-NO$, $-NO_2$, $-N_3$, $-SO_2R^{70}$, $-SO_3^-M^+$, $-SO_3R^{70}$, $-OSO_2R^{70}$, $-OSO_3^-M^+$, $-OSO_3R^{70}$, $-PO_3^{-2}(M^+)_2$, $-P(O)(OR^{70})O^-M^+$, $-P(O)(OR^{70})_2$, $-C(O)R^{70}$, $-C(S)R^{70}$, $-C(NR^{70})R^{70}$, $-CO_2^-M^+$, $-CO_2R^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OCO_2^-M^+$, $-OCO_2R^{70}$, $-OC(S)OR^{70}$, $-NR^{70}C(O)R^{70}$, $-NR^{70}C(S)R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not $-O^-M^+$, $-OR^{70}$, $-SR^{70}$, or $-S^-M^+$.

In addition to the groups disclosed with respect to the individual terms herein, substituent groups for hydrogens on nitrogen atoms in "substituted" heteroalkyl and cycloheteroalkyl groups are, unless otherwise specified, $-R^{60}$, $-O^-M^+$, $-OR^{70}$, $-SR^{70}$, $-S^-M^+$, $-NR^{80}R^{80}$, trihalomethyl, $-CF_3$, $-CN$, $-NO$, $-NO_2$, $-S(O)_2R^{70}$, $-S(O)_2O^-M^+$, $-S(O)_2OR^{70}$, $-OS(O)_2R^{70}$, $-OS(O)_2O^-M^+$, $-OS(O)_2OR^{70}$, $-P(O)(O^-)_2(M^+)_2$, $-P(O)(OR^{70})O^-M^+$, $-P(O)(OR^{70})(OR^{70})$, $-C(O)R^{70}$, $-C(S)R^{70}$, $-C(NR^{70})R^{70}$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O)OR^{70}$, $-OC(S)OR^{70}$, $-NR^{70}C(O)R^{70}$, $-NR^{70}C(S)R^{70}$, $-NR^{70}C(O)OR^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

DETAILED DESCRIPTION

Before the present compounds and methods are described, it is to be understood that this invention is not limited to particular compounds and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Metabolism-Resistant Fenfluramine Analogs

The present disclosure is related to structural and/or functional analogs of fenfluramine that are resistant to systemic metabolism. As used herein, the term "fenfluramine analog" refers to a structural and/or functional analog of fenfluramine Functional analogs of fenfluramine are not necessarily structural analogs. Unless explicitly stated, as used herein a fenfluramine analog includes both functional and structural analogs. In some cases, the subject fenfluramine analogs are resistant to metabolism to de-ethylated norfenfluramine analogs in vivo.

Fenfluramine is an effective appetite suppressant drug that was withdrawn from the drug market because of increased incidents of heart disease. Fenfluramine is metabolized in vivo into norfenfluramine. Such metabolism includes cleavage of an N-ethyl group to produce norfenfluramine as shown below.

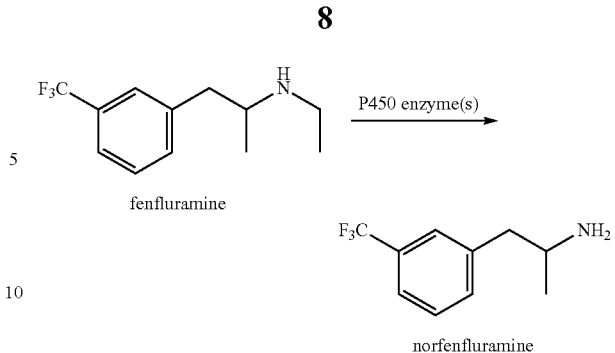

De-ethylated norfenfluramine metabolite can have undesirable biological activities that cause side effects such as increased pulmonary hypertension and aortic valvular disease.

The present disclosure provides compounds that are stabilized against such undesirable metabolism. As used herein, the term "metabolism-resistant" refers to a stability of a fenfluramine against any of the metabolic pathways of fenfluramine that reduces the intended pharmacologic effect of the compound. One metabolic pathway of interest against which the subject compounds can resistant is the deethylation that can occur via P450 enzyme(s) in the liver. In some cases, the fenfluramine analog is referred to as being metabolically stable.

Metabolism into Norfenfluramine

Fenfluramine is metabolized in vivo into norfenfluramine by metabolizing enzymes such as cytochrome P450 enzymes in the liver. The enzymes in human liver that convert fenfluramine to norfenfluramine include CYP1A2, CYP2B6, and CYP2D6; CYP2C9, CYP2C19, and CYP3A4 also play a role.

Fenfluramine Analogs

Aspects of the present disclosure include analogs of fenfluramine that are resistant to N-dealkylation, e.g., via action of metabolizing enzymes (e.g., as described herein). In some embodiments, the fenfluramine analogs are resistant to cytochrome P450 enzymes. In certain cases, the fenfluramine analogs are resistant to a P450 enzyme selected from CYP2D6, CYP2C19, CYP1A2, CYP2B6, CYP3A4 and CYP2C9. In certain cases, the fenfluramine analogs are resistant to a P450 enzyme selected from CYP1A2, CYP2B6 and CYP2D6. In some instances, the subject fenfluramine analogs include a secondary, tertiary or quaternary amino group that is stabilized against de-alkylation to a primary amine in vivo.

In some cases, the analogs are fluorinated compounds, e.g., analogs of fenfluramine that include one or more fluorine substituents. In some instances, the analogs include fluorine substituents at position(s) adjacent to the amine nitrogen of fenfluramine By "adjacent to" is meant substitution at a carbon atom position that is located alpha, beta or gamma to the amine nitrogen. In some embodiments, the fenfluramine analog further includes one or more additional non-fluorine substituents which impart upon the compound resistance to cytochrome P450 enzymes. In certain cases, the fenfluramine analogs further includes one or more additional non-fluorine substituents which impart upon the compound resistance to a P450 enzyme selected from CYP2D6, CYP2C19, CYP1A2, CYP2B6 CYP3A4 and CYP2C9. In certain cases, the fenfluramine analogs further includes one or more additional non-fluorine substituents which impart upon the compound resistance to a P450 enzyme selected from CYP1A2, CYP2B6 and CYP2D6. In certain instances, the analog further includes one or more additional non-fluorine substituents which impart upon the compound resistance to CYP2D6 metabolism.

In general terms, changes in pKa can have a predominant effect on P450 enzyme (e.g., CYP2D6) substrate binding. P450 enzyme substrates that include more basic amine groups are associated with higher affinities and catalytic efficiencies. The present disclosure provides fluorine substituted analogs where the pKa of the amino group is lowered (i.e., lower basicity) relative to the amine group of fenfluramine.

In addition, high lipophilicity of substituent groups in a metabolizing enzyme, such as a P450 enzymes can be associated with high affinity and catalytic efficiencies. In certain cases, the a P450 enzyme is selected from CYP2D6, CYP2C19, CYP1A2, CYP2B6 CYP3A4 and CYP2C9. The present disclosure provides substituted analogs of fenfluramine which include one or more hydrophilic substituents not present in fenfluramine which impart on the compound a desirable reduced liphophilicity.

Deuteration of biologically active compounds of interest can produce analogs with improved pharmacokinetics (PK), pharmacodynamics (PD), and/or toxicity profiles. In some embodiments, fenfluramine analogs of interest include a deuterium substituent at any convenient location (e.g., as described herein) adjacent to the amine nitrogen atom. In certain instances, the fenfluramine analog includes 2 or more deuterium substituents, such as 3 or more, 4 or more, or 5 or more deuterium substituents. In some cases, the deuterium substituents are located on carbon atoms adjacent to the amino N atoms on the compound, e.g., the alpha-carbon atom. In some cases, the two or more deuterium substituents are located on the same carbon atom adjacent to the amino nitrogen.

Other modifications of interest that can be incorporated into the subject fenfluramine analogs include, but are not limited to, replacement of the —CF$_3$ aryl substituent of fenfluramine, e.g., with an isosteric or isoelectronic group, and introduction of quaternary amino group. In some instances, the fenfluramine includes a —SF$_5$ aryl substituent. In certain instances, the fenfluramine analog is an N-alkylated analog where the amine nitrogen is a quatery amine, i.e., a positively charged ammonium group. In some embodiments, the analog includes an N-methylated amine group.

Aspects of the present disclosure include fenfluramine analogs including an additional substituent on the amino N atom that sterically hinders the binding of the compound to a metabolizing enzyme. Any convenient substituents may be included at the N atom of the subject compounds to provide a sterically bulky group. In some cases, the N-substituent of interest is a N-alkyl or N-substituted alkyl group. In some cases, the N-substituent is a N-aryl, N-heteroaryl, N-substituted aryl or N-substituted heteroaryl group. Substituents of interest include, but are not limited to, methyl, ethyl, propyl, isopropyl, butyl, tert-butyl, trifluoromethyl, phenyl, benzyl and substituted benzyl. In some embodiments, the analog includes an N-t-butyl group.

In some embodiments, the fenfluramine analog is a compound having the formula (I):

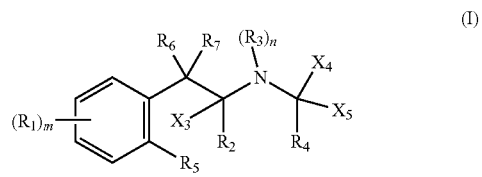

wherein:

$R_1$, $R_2$, $R_3$, $R_4$, $R_5$, $R_6$ and $R_7$ are independently selected from hydrogen, halogen, $X_1$, $X_2$, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl, substituted heterocycle, or together with a second $R^1$-$R^7$ group form a cycloalkyl ring, a heterocycle ring, an aryl ring or a heteroaryl ring that is optionally substituted wherein $R_2$ and $R_5$, $R_2$ and $R_4$, $R_1$ and $R_5$, $R_6$ and $R_7$, and/or $R_3$ and $R_6$ are cyclically linked;

$X_1$-$X_5$ are each independently H, D, F, alkyl or substituted alkyl;

m is 0-4; and n is 1 or 2, wherein when n is 2 the nitrogen is positively charged;

or a salt thereof.

In some embodiments of formula (I), $R_2$ and $R_5$ are cyclically linked together to form a cycloalkyl ring, a heterocycle ring, an aryl ring or a heteroaryl ring that is optionally substituted. In some embodiments of formula (I), $R_2$ and $R_4$ are cyclically linked together to form a cycloalkyl ring, a heterocycle ring, an aryl ring or a heteroaryl ring that is optionally substituted. In some embodiments of formula (I), $R_1$ and $R_5$ are cyclically linked together to form a cycloalkyl ring, a heterocycle ring, an aryl ring or a heteroaryl ring that is optionally substituted. In some embodiments of formula (I), $R_6$ and $R_7$ are cyclically linked together to form a cycloalkyl ring, a heterocycle ring, an aryl ring or a heteroaryl ring that is optionally substituted. In some embodiments of formula (I), $R_3$ and $R_6$ are cyclically linked together to form a cycloalkyl ring, a heterocycle ring, an aryl ring or a heteroaryl ring that is optionally substituted.

In some embodiments, the fenfluramine analog is a compound having the formula (II):

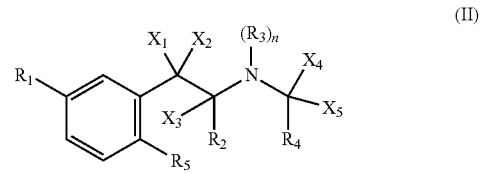

wherein:

$R_1$ is an alkyl, a substituted alkyl (e.g., CF$_3$) or SF$_5$;

$R_2$, $R_3$, $R_4$ and $R_5$ are independently selected from hydrogen, halogen, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl and substituted heterocycle, where $R_2$ and $R_5$ or $R_2$ and $R_4$ are optionally cyclically linked;

$X_1$-$X_5$ are each independently H, D, F, alkyl or substituted alkyl; and n is 1 or 2, wherein when n is 2 the nitrogen is positively charged;

or a salt thereof. In some embodiments of formula (I)-(II), $R_2$ and $R_4$ are independently selected from hydrogen, alkyl, substituted alkyl, aryl, substituted aryl, heterocycle, heteroaryl, substituted heteroaryl and substituted heterocycle. In some embodiments of formula (II), $R_2$ and $R_5$ are cyclically linked together to form a cycloalkyl ring, a heterocycle ring, an aryl ring or a heteroaryl ring that is optionally substituted. In some embodiments of formula (II), $R_2$ and $R_4$ are cyclically linked together to form a cycloalkyl ring, a heterocycle ring, an aryl ring or a heteroaryl ring that is optionally substituted. In certain cases, $R_2$ is cyclically linked to $R_5$, e.g., to form a 5, 6 or 7-membered carbocyclic or heterocyclic ring, which may be saturated or unsaturated. In some embodiments of formula (I)-(II), $R_5$ is selected from hydrogen, halogen, alkoxy, acyl, substituted acyl, carboxy, cyano, substituted alkoxy, alkyl and substituted alkyl. In certain cases, $R_5$ is cyclically linked to $R_2$, e.g., to form a 5, 6 or 7-membered carbocyclic or heterocyclic ring, which may be saturated or unsaturated. In some embodiments of formula (I)-(II), each $R_3$ is selected from hydrogen, alkyl and substituted alkyl. In some embodiments of formula (I)-(II), n is 1. In some embodiments of formula (I)-(II), n is 2. In some embodiments of formula (I), $R_3$ is H. In some embodiments of formula (I)-(II), $R_3$ is H. In some cases, $R_3$ is selected from heteroaryl, substituted aryl, substituted heteroaryl. In some cases, $R_3$ is selected from methyl, ethyl, propyl, isopropyl, butyl, tert-butyl, trifluoromethyl, phenyl, benzyl and substituted benzyl. In some embodiments of formula (I)-(II), $R_3$ is t-butyl and n is 1.

In some embodiments of Formulae (I)-(II), the fenfluramine analog has the formula (III):

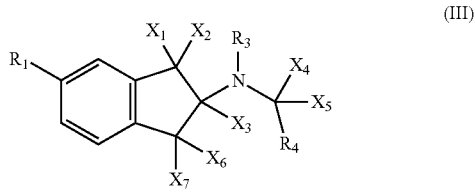

wherein $X_1$-$X_7$ are each independently H, D or F, and $R_1$, $R_3$ and $R_4$ are as defined in any of the embodiments of formula (I). In some embodiments of formula (III), $R_3$ is selected from hydrogen, alkyl and substituted alkyl. In some embodiments of formula (III), $R_3$ is H. In some embodiments of formula (III), $R_3$ is selected from heteroaryl, substituted aryl, substituted heteroaryl. In some cases, $R_3$ is selected from methyl, ethyl, propyl, isopropyl, butyl, tert-butyl, trifluoromethyl, phenyl, benzyl and substituted benzyl. In some embodiments of formula (III), $R_3$ is t-butyl.

In some embodiments of formula (III), $X_1$-$X_7$ are each independently H or F. In some embodiments of formula (III), at least one of $X_1$-$X_7$ is F. In some embodiments of formula (III), at least two of $X_1$-$X_7$ is F. In some embodiments of formula (III), at least three of $X_1$-$X_7$ is F. In some embodiments of formula (III), at least four of $X_1$-$X_7$ is F. In some embodiments of formula (III), at least five of $X_1$-$X_7$ is F. In some embodiments of formula (III), at least six of $X_1$-$X_7$ is F.

In some embodiments of formula (III), $X_1$-$X_7$ are each independently H or D. In some embodiments of formula (III), at least one of $X_1$-$X_7$ is D. In some embodiments of formula (III), at least two of $X_1$-$X_7$ is D. In some embodiments of formula (II), at least three of $X_1$-$X_7$ is D. In some embodiments of formula (III), at least four of $X_1$-$X_7$ is D. In some embodiments of formula (III), at least five of $X_1$-$X_7$ is D. In some embodiments of formula (III), at least six of $X_1$-$X_7$ is D.

In some embodiments of Formulae (I)-(II), the fenfluramine analog has the formula (IV):

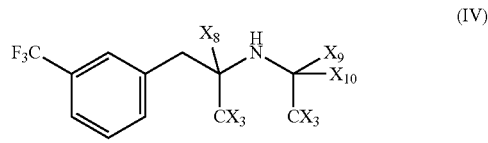

wherein $X_8$-$X_{10}$ and each X are independently H, D or F, provided at least one $X_8$-$X_{10}$ or X is F. In some embodiments of Formula (IV), each X is F. In some embodiments of Formula (IV), each X is D. In some embodiments of Formula (IV), each X is H. In some embodiments of Formula (IV), each X is F. In some embodiments of Formula (IV), $X_8$ is F. In some embodiments of Formula (IV), $X_9$ and $X_{10}$ are each F.

In some embodiments of Formula (IV), the fenfluramine analog has one of the following structures:

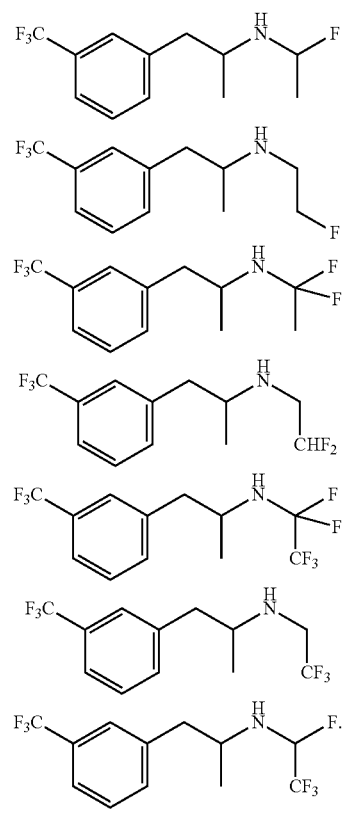

In some embodiments of Formula (I), the fenfluramine analog has one of the formulae (IVa)-(IVc):

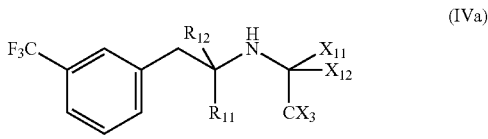

-continued

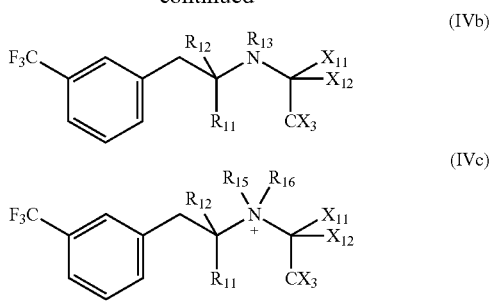

wherein $X_{11}$, $X_{12}$ and each X is independently H, D or F; and
$R_{11}$-$R_{16}$ are each independently an alkyl or a substituted alkyl.

In some embodiments of formulae (IVa)-(IVc), each X is F. In some embodiments of formulae (IVa)-(IVc), $X_{11}$ is F and $X_{12}$ is H. In some embodiments of formulae (IVa)-(IVc), $X_{11}$ is F and $X_{12}$ is F. In some embodiments of formulae (IVa)-(IVc), $X_{11}$ is F and $X_{12}$ is D. In some embodiments of formulae (IVa)-(IVc), $X_{11}$ is D and $X_{12}$ is D. In some embodiments of formulae (IVa)-(IVc), $R_{11}$ is a substituted alkyl (e.g., as described herein). In some embodiments of formulae (IVa)-(IVc), $R_{12}$ is a substituted alkyl (e.g., as described herein). In some embodiments of formulae (IVa)-(IVc), $R_{13}$ is selected from methyl, ethyl, propyl, isopropyl, butyl, tert-butyl, trifluoromethyl, phenyl, benzyl and substituted benzyl. In some embodiments of formulae (IVa)-(IVc), $R_{13}$ is a tert-butyl. In some embodiments of formulae (IVa)-(IVc), $R_{15}$ and $R_{16}$ are each an alkyl, such as methyl.

In some embodiments of Formula (I), the fenfluramine analog has the formula (V):

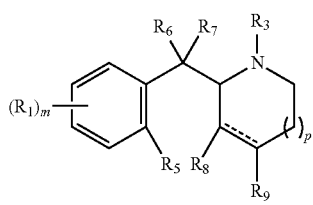

wherein $R_1$, $R_3$, $R_5$, $R_6$, $R_7$ and m are as defined above, p is 0, 1 or 2, and $R_8$ and $R_9$ are independently selected from hydrogen, halogen, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl and substituted heterocycle, or $R_8$ and $R_9$ are cyclically linked to form a 5 or 6-membered cycloalkyl, heterocycle, aryl or heteroaryl ring, that is optionally further substituted, where the dashed bond represents a single or double covalent bond.

In some embodiments of Formula (V), $R^8$ and $R^9$ are not cyclically linked. In some embodiments of Formula (V), p is 0. In some embodiments of Formula (V), p is 1. In some embodiments of Formula (V), p is 2. In some embodiments of formula (V), each $R_1$ is independently selected from halogen, $CF_3$, $SF_5$ acyl, substituted acyl, carboxy, alkyl ester, substituted alkyl ester, cyano, hydroxy, alkoxy, substituted alkoxy, alkyl, substituted alkyl; $R_7$ is hydrogen, hydroxy, alkoxy, substituted alkoxy, alkylcarbonyloxy, or substituted alkyl carbonyloxy; $R_3$ is hydrogen, alkyl or substituted alkyl; m is 0-4; and p is 0 or 1. In some embodiments of Formula (V), $R_6$ is aryl or substituted aryl. In some embodiments of Formula (V), $R_6$ is phenyl or substituted phenyl. In some embodiments of Formula (V), $R_6$ is heteroaryl or substituted heteroaryl.

In some embodiments of Formula (V), $R^8$ and $R^9$ are cyclically linked and together form an aryl or substituted aryl ring, e.g., a fused benzene ring. In some embodiments of Formula (V), $R_6$ are $R_6$ are hydrogen, fluoro or deuteron. In some embodiments of Formula (V), $R_6$ are $R_6$ are hydrogen.

In some embodiments of Formula (V), $R^8$ and $R^9$ are cyclically linked and together form an aryl or substituted aryl ring, and $R_8$ and $R_5$ are also cyclically linked and together form a 6-membered carbocycle ring, e.g., a partially unsaturated fused ring. In some cases, the compound includes a 4-ring system of fused carbocyclic and heterocyclic rings. In some embodiments of Formula (V), $R_6$ are $R_6$ are hydrogen, fluoro or deuterium. In some embodiments of Formula (V), $R_6$ are $R_6$ are hydrogen.

In some embodiments of Formula (V), the fenfluramine analog has the formula (VI):

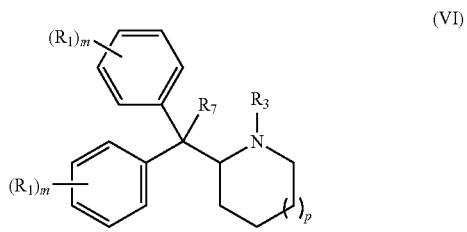

wherein $R_1$, $R_3$, $R_7$, and m are as defined above, and p is 0, 1 or 2.

In some embodiments of formula (VI), each $R_1$ is independently selected from halogen, $CF_3$, $SF_5$, acyl, substituted acyl, carboxy, alkyl ester, substituted alkyl ester, cyano, hydroxy, alkoxy, substituted alkoxy, alkyl, substituted alkyl; $R_7$ is hydrogen, hydroxy, alkoxy, substituted alkoxy, alkylcarbonyloxy, or substituted alkyl carbonyloxy; $R_3$ is hydrogen, alkyl or substituted alkyl; each m is 0-4; and p is 0 or 1. In certain embodiments of formula (VI), each $R_1$ is independently selected from halogen, $CF_3$, $SF_5$, carboxy, cyano, hydroxy, alkoxy, substituted alkoxy, alkyl, substituted alkyl; $R_7$ is hydrogen or hydroxy; $R_3$ is hydrogen, alkyl or substituted alkyl; each m is 0, 1 or 2; and p is 0 or 1. In certain embodiments of formula (VI), $R_7$ is hydrogen or hydroxy; $R_3$ is hydrogen, alkyl or substituted alkyl; each m is 0; and p is 0 or 1. In certain embodiments of formula (VI), $R_7$ is hydrogen. In certain embodiments of formula (VI), $R_7$ is hydroxy. In certain embodiments of formula (VI), $R_3$ is hydrogen. In certain embodiments of formula (VI), $R_3$ is alkyl or substituted alkyl. In certain embodiments of formula (VI), each m is 0. In certain embodiments of formula (VI), p is 0. In certain embodiments of formula (VI), p is 1.

In certain embodiments of formula (VI), the fenfluramine analog has one of the following structures:

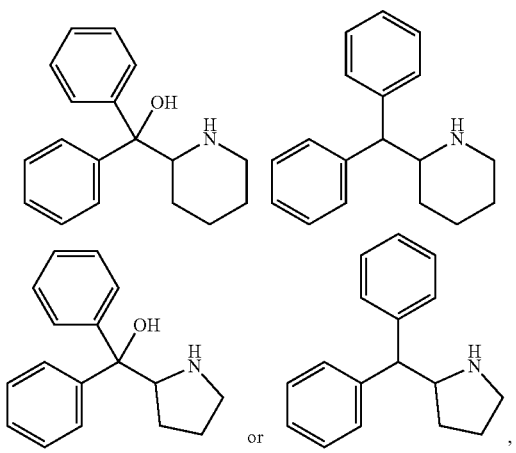

or a prodrug thereof, or a stereoisomer thereof, or a salt thereof.

In some embodiments of formula (V), the fenfluramine analog has formula (VII):

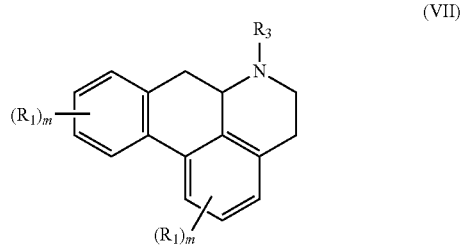

or a prodrug thereof, or a stereoisomer thereof, or a salt thereof.

In certain embodiments of formula (VII), each $R_1$ is independently selected from halogen, $CF_3$, $SF_5$, carboxy, cyano, hydroxy, alkoxy, substituted alkoxy, alkyl, substituted alkyl; $R_7$ is hydrogen or hydroxy; $R_3$ is hydrogen, alkyl or substituted alkyl; and each m is 0, 1 or 2. In certain embodiments of formula (VII), $R_3$ is hydrogen, alkyl or substituted alkyl; and each m is 0. In certain embodiments of formula (VII), $R_3$ is hydrogen. In certain embodiments of formula (VII), $R_3$ is alkyl or substituted alkyl. In certain embodiments of formula (VII), each m is 0.

In certain embodiments of formula (VII), the fenfluramine analog has the structure:

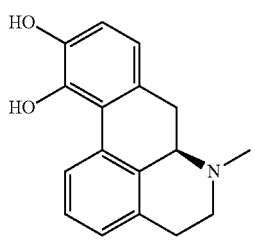

or a prodrug thereof, or a stereoisomer thereof, or a salt thereof.

In certain instances, the fenfluramine analog is apomorphine or a structural analog or derivative thereof. Apomorphine structural analogs and derivatives of interest, include but are not limited to, those compounds described in EP1496915 by Holick et al. In certain instances, the fenfluramine analog is N-propylnorapomorphine.

In some embodiments of Formula (I), the fenfluramine analog has the formula (VIII):

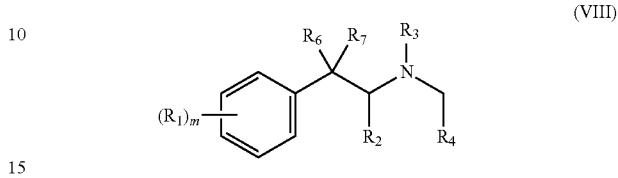

wherein $R_1$-$R_4$, $R_6$, $R_7$ and m are as defined above.

In certain embodiments of formula (VIII), each $R_1$ is independently selected from halogen, $CF_3$, $SF_5$, carboxy, cyano, hydroxy, alkoxy, substituted alkoxy, alkyl, substituted alkyl; and m is 0, 1 or 2. In certain embodiments of formula (VIII), $R_3$ is hydrogen, alkyl or substituted alkyl. In certain embodiments of formula (VIII), $R_3$ is hydrogen. In certain embodiments of formula (VIII), $R_3$ is alkyl or substituted alkyl. In certain embodiments of formula (VIII), m is 0. In certain embodiments of formula (VIII), m is 1 and $R_1$ is a 4-substituent. In certain embodiments of formula (VIII), $R_7$ is hydrogen. In certain embodiments of formula (VIII), $R_2$ is alkyl or substituted alkyl. In certain embodiments of formula (VIII), $R_2$ is hydrogen. In certain embodiments of formula (VIII), $R_4$ is hydrogen. In certain embodiments of formula (VIII), $R_4$ is alkyl or substituted alkyl. In certain embodiments of formula (VIII), $R_6$ is a cycloalkyl, a substituted cycloalkyl, an aryl, a substituted aryl, a heterocycle or a substituted heterocycle. In certain embodiments of formula (VIII), $R_6$ and $R_7$ are cyclically linked to form a 4, 5 or 6-membered cycloalkyl ring, optionally substituted with one or more $R_1$.

In some embodiments of Formula (I) and (VIII), the fenfluramine analog has the formula (IX):

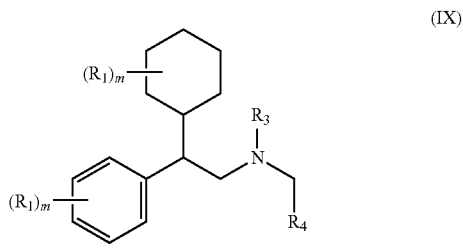

wherein $R_1$, $R_3$, $R_4$, and each m are as defined above.

In certain embodiments of formula (IX), each $R_1$ is independently selected from halogen, $CF_3$, $SF_5$, carboxy, cyano, hydroxy, alkoxy, substituted alkoxy, alkyl, substituted alkyl; and each m is 0, 1 or 2. In certain embodiments of formula (IX), $R_3$ is hydrogen, alkyl or substituted alkyl. In certain embodiments of formula (IX), $R_3$ is hydrogen. In certain embodiments of formula (IX), $R_3$ is alkyl or substituted alkyl. In certain embodiments of formula (IX), each m is 0 or 1. In certain embodiments of formula (IX), each m is 0 or 1 and $R_1$ is a 4-substituent. In certain embodiments of formula (IX), $R_4$ is hydrogen. In certain embodiments of formula (IX), $R_4$ is alkyl or substituted alkyl.

In certain embodiments, the fenfluramine analog is Desvenlafaxine or a structural analog or derivative thereof. In certain embodiments, the fenfluramine analog is Desvenlafaxine or O-desmethylvenlafaxine. In certain embodiments of formula (VII), the fenfluramine analog has the structure:

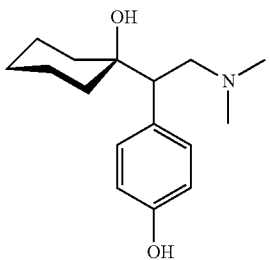

or a prodrug thereof, or a stereoisomer thereof, or a salt thereof.

In some embodiments of Formula (I) and (VIII), the fenfluramine analog has the formula (X):

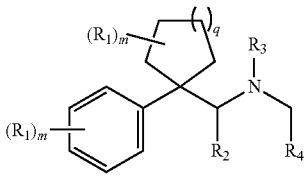

wherein $R_1$-$R_4$, and each m are as defined above, and q is 0, 1 or 2.

In certain embodiments of formula (X), each $R_1$ is independently selected from halogen, $CF_3$, $SF_5$, carboxy, cyano, hydroxy, alkoxy, substituted alkoxy, alkyl, substituted alkyl; and each m is 0, 1 or 2. In certain embodiments of formula (X), $R_2$ is alkyl or substituted alkyl. In certain embodiments of formula (X), $R_2$ is hydrogen. In certain embodiments of formula (X), $R_3$ is hydrogen, alkyl or substituted alkyl. In certain embodiments of formula (X), $R_3$ is hydrogen. In certain embodiments of formula (X), $R_3$ is alkyl or substituted alkyl. In certain embodiments of formula (X), each m is 0 or 1. In certain embodiments of formula (X), each m is 0 or 1 and $R_1$ is a 4-substituent. In certain embodiments of formula (X), $R_4$ is hydrogen. In certain embodiments of formula (X), $R_4$ is alkyl or substituted alkyl.

In some embodiments of Formula (X), the fenfluramine analog has the formula (XIa) or (XIb):

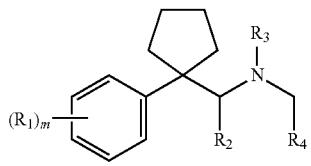

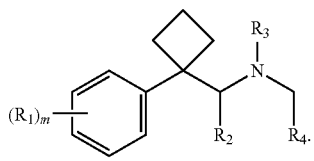

In certain embodiments of formulae (XIa)-(XIb), each $R_1$ is independently selected from halogen, $CF_3$, $SF_5$, carboxy, cyano, hydroxy, alkoxy, substituted alkoxy, alkyl, substituted alkyl; and m is 0, 1 or 2. In certain embodiments of formula (XIa)-(XIb), each $R_1$ is independently selected from halogen, $CF_3$, $SF_5$ and hydroxy; and m is 0 or 1. In certain embodiments of formula (XIa)-(XIb), $R_2$ is alkyl or substituted alkyl. In certain embodiments of formula (XIa)-(XIb), $R_2$ is hydrogen. In certain embodiments of formula (XIa)-(XIb), $R_3$ is hydrogen. In certain embodiments of formula (XIa)-(XIb), $R_3$ is alkyl or substituted alkyl. In certain embodiments of formula (XIa)-(XIb), each m is 0 or 1. In certain embodiments of formula (XIa)-(XIb), each m is 0 or 1 and $R_1$ is a 4-substituent. In certain embodiments of formula (XIa)-(XIb), $R_4$ is hydrogen. In certain embodiments of formula (XIa)-(XIb), $R_4$ is alkyl or substituted alkyl.

In certain instances, the fenfluramine analog is sibutramine or a structural analog or derivative thereof. Sibutramine structural analogs and derivatives of interest, include but are not limited to, didesmethyl sibutramine. In certain embodiments of formula (XIb), the fenfluramine analog has the structure:

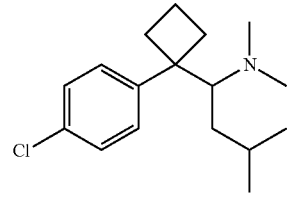 [SMILES: CC(C)CC(N(C)C)C1(c2ccc(Cl)cc2)CCC1]

or a prodrug thereof, or a stereoisomer thereof, or a salt thereof.

Preparation of Fenfluramine Compounds

Any convenient methods of preparing fenfluramine can be adapted in the preparation of the subject compounds. Exemplary methods of interest which can be adapted for use in the preparation of the subject fenfluramine analogs are described below.

Fenfluramine has been synthesized in many ways, some going through the synthesis of the intermediate 1-(3-trifluoromethyl)phenyl-propan-2-one. This U.S. Pat. No. 3,198,833 describes some syntheses of this ketone starting from 3-trifluoromethylphenylacetonitrile or from the corresponding alcohol.

Fenfluramine can be obtained from 1-(3-trifluoromethyl)phenyl-propan-2-one through reductive amination with an amine, for instance as described in Hungarian Patent HU T055343.

U.S. Pat. No. 5,811,586 describes a process for manufacturing 1-(3-trifluoromethyl)phenyl-propan-2-one intermediate in the synthesis of fenfluramine that includes reacting the diazonium salt of 3-trifluoromethylaniline with isopropenyl acetate in a polar solvent in the presence of a catalytic amount of a cuprous salt and, optionally, of a base and purifying the crude product through the bisulfite complex or distillation under vacuum.

Methods of Use

The above-described compounds may be employed in a variety of methods. As summarized above, aspects of the method include administering to a subject in need thereof a therapeutically effective amount of a fenfluramine analog (e.g., a structural or functional analog of fenfluramine as described herein) to treat or prevent a disease or condition of interest. By "therapeutically effective amount" is meant the concentration of a compound that is sufficient to elicit the desired biological effect (e.g., treatment or prevention of epilepsy). Diseases and conditions of interest include, but are not limited to, epilepsy, particularly intractable forms of epilepsy including Dravet syndrome, Lennox Gastaut syndrome and Doose syndrome, neurological related diseases, obesity and obesity related diseases.

In some embodiments, the subject method includes administering to a subject a subject compound to treat a neurological related disease. Neurological related diseases of interest include, but are not limited to, epilepsy, and severe myoclonic epilepsy in infancy (Dravet syndrome), Lennox-Gastaut syndrome and Doose syndrome. In certain embodiments, the subject is human. In certain instances, the subject suffers from Dravet syndrome. In certain embodiments, the compound is administered as a pharmaceutical preparation.

Thus, according to a still further aspect of the present invention, there is provided a method of stimulating one or more 5-HT receptors in the brain of a patient by administering an effective dose of a fenfluramine analog to said patient, said one or more 5-HT receptors being selected from one or more of $5\text{-}HT_1$, $5\text{-}HT_{1A}$, $5\text{-}HT_{1B}$, $5\text{-}HT_{1C}$, $5\text{-}HT_{1D}$, $5\text{-}HT_{1E}$, $5\text{-}HT_{1F}$, $5\text{-}HT_2$, $5\text{-}HT_{2A}$, $5\text{-}HT_{2B}$, $5\text{-}HT_{2C}$, $5\text{-}HT_3$, $5\text{-}HT_4$, $5\text{-}HT_5$, $5\text{-}HT_{5A}$, $5\text{-}HT_{5B}$ $5\text{-}HT_6$, and $5\text{-}HT_7$ amongst others. In certain embodiments of this aspect of the invention, the patient has been diagnosed with Dravet Syndrome.

In embodiments of the invention, any effective dose of the fenfluramine analog can be employed. In certain embodiments, a daily dose of less than about 10 mg/kg/day is employed, such as about 9 mg/kg/day, about 8 mg/kg/day, about 7 mg/kg/day, about 6 mg/kg/day, about 5 mg/kg/day, about 4 mg/kg/day, about 3 mg/kg/day, about 2 mg/kg/day, about 1 mg/kg/day, about 0.9 mg/kg/day, about 0.8 mg/kg/day, about 0.7 mg/kg/day, about 0.6 mg/kg/day, or about 0.5 mg/kg/day is employed. In some cases, a daily dose of between about 1 mg/kg/day and about 10 mg/kg/day is employed, such as between about 2 mg/kg/day and about 10 mg/kg/day, between about 3 mg/kg/day and about 10 mg/kg/day, between about 4 mg/kg/day and about 10 mg/kg/day, or between about 5 mg/kg/day and about 10 mg/kg/day. In some cases, a daily dose of between about 0.5 mg/kg/day and about 1.0 mg/kg/day is employed. In certain embodiments, a daily dose of less than about 1.0 mg/kg/day is employed. In some cases, a preferred dose is less than about 0.5 to about 0.01 mg/kg/day.

As indicated above the dosing is based on the weight of the patient. However, for convenience the dosing amounts may be preset such as in the amount of 1 mg, 2.5 mg, 5 mg, 10 mg, 15 mg, 20 mg, 30 mg, 40 mg, or 50 mg. In general the smallest dose which is effective should be used for the particular patient.

The dose of fenfluramine analog administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

Administration of the subject compounds may be systemic or local. In certain embodiments, administration to a mammal will result in systemic release of a subject compound (for example, into the bloodstream). Methods of administration can include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the subject compounds and compositions are administered orally. In certain embodiments, it may be desirable to administer a compound locally to the area in need of treatment. In some embodiments, the method of administration of the subject compound is parenteral administration. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In some embodiments, the subject method includes administering to a subject an appetite suppressing amount of the subject compound to treat obesity. Any convenient methods for treating obesity may be adapted for use with the subject fenfluramine analogs. Any of the pharmaceutical compositions described herein can find use in treating a subject for obesity. Combination therapy includes administration of a single pharmaceutical dosage formulation which contains the subject compound and one or more additional agents; as well as administration of the subject compound and one or more additional agent(s) in its own separate pharmaceutical dosage formulation. For example, a subject compound and an additional agent active with appetite suppressing activity (e.g., phentermine or topiramate) can be administered to the patient together in a single dosage composition such as a combined formulation, or each agent can be administered in a separate dosage formulation. Where separate dosage formulations are used, the subject compound and one or more additional agents can be administered concurrently, or at separately staggered times, e.g., sequentially. In some embodiments, the method further includes co-administering to the subject with the subject fenfluramine analog, an antiepileptic agent. Antiepileptic agents of interest that find use in methods of co-administering include, but are not limited to, Acetazolamide, Carbamazepine, Clobazam, Clonazepam, Eslicarbazepine acetate, Ethosuximide, Gabapentin, Lacosamide, Lamotrigine, Levetiracetam, Nitrazepam, Oxcarbazepine, Perampanel, Piracetam, Phenobarbital, Phenytoin, Pregabalin, Primidone, Retigabine, Rufinamide, Sodium valproate, Stiripentol, Tiagabine, Topiramate, Vigabatrin and Zonisamide.

In some embodiments, the subject method is an in vitro method that includes contacting a sample with a subject compound. The protocols that may be employed in these methods are numerous, and include but are not limited to, serotonin release assays from neuronal cells, cell-free assays, binding assays (e.g., 5HT2B receptor binding assays); cellular assays in which a cellular phenotype is measured, e.g., gene expression assays; and assays that involve a particular animal model for a condition of interest (e.g., Dravet syndrome, Lennox-Gastaut syndrome or Doose syndrome).

Pharmaceutical Preparations

Also provided are pharmaceutical preparations. Pharmaceutical preparations are compositions that include a compound (either alone or in the presence of one or more additional active agents) present in a pharmaceutically acceptable vehicle. The term "pharmaceutically acceptable" means approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal.

The choice of excipient will be determined in part by the particular compound, as well as by the particular method used to administer the composition. Accordingly, there is a wide variety of suitable formulations of the pharmaceutical composition of the present invention.

The dosage form of a fenfluramine analog employed in the methods of the present invention can be prepared by combining the fenfluramine analog with one or more pharmaceutically acceptable diluents, carriers, adjuvants, and the like in a manner known to those skilled in the art of pharmaceutical formulation.

By way of illustration, the fenfluramine analog can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as solubilizers, isotonic agents, suspending agents, emulsifying agents, stabilizers, preservatives, colorants, diluents, buffering agents, surfactants, moistening agents, flavoring agents and disintegrators, and including, but not limited to, corn starch, gelatin, lactose, dextrose, sucrose, microcrystalline cellulose, kaolin, mannitol, dicalcium phosphate, sodium chloride, alginic acid, vegetable or other similar oils, synthetic aliphatic acid glycerides, esters of higher aliphatic acids or propylene glycol, corn starch, potato starch, acacia, tragacanth, gelatin, glycerin, sorbitol, ethanol, polyethylene glycol, colloidal silicon dioxide, croscarmellose sodium, talc, magnesium stearate and stearic acid. Disintegrators commonly used in the formulations of this invention include croscarmellose, microcrystalline cellulose, corn starch, sodium starch glycolate and alginic acid. The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

In some cases, the compound is formulated for oral administration. In some cases, for an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers.

Particular formulations of the invention are in a liquid form. The liquid may be a solution or suspension and may be an oral solution or syrup which is included in a bottle with a pipette which is graduated in terms of milligram amounts which will be obtained in a given volume of solution. The liquid solution makes it possible to adjust the solution for small children which can be administered anywhere from 0.5 mg to 15 mg and any amount between in half milligram increments and thus administered in 0.5, 1.0, 1.5, 2.0 mg, etc.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Preparation of 1-(3-Trifluoromethyl)phenyl-propan-2-one 35 mL of water and 45 g of 37% (w/w) aqueous hydrochloric acid are put in a flask equipped with stirrer and dropping funnel. 24.25 Grams (0.151 moles) of m-trifluoromethylaniline are added after having cooled to 10 degree C. with an ice bath and then, at 5 degree C., an aqueous solution containing 12.43 g (0.180 moles) of sodium nitrite in 150 ml of water is slowly added. The reaction mixture is stirred for 30 minutes and then is poured during 30 minutes into a mixture made by 90 ml of water, 1.35 g (0.014 moles) of cuprous chloride, 2.30 g (0.013 moles) of cupric chloride dihydrate, 50 ml of acetone, 40.8 g (0.300 moles) of sodium acetate trihydrate and 23 g (0.230 moles) of isopropenyl acetate while keeping the reaction temperature at 30 degree C. After further 30 minutes of stirring, the reaction mixture is brought to 20 degree C., 50 ml of methylene chloride are added and the two layers are separated.

The aqueous layer is discarded while the organic layer is concentrated under vacuum until an oil is obtained which is treated with 35 g of sodium metabisulfite, 70 ml of water and 150 ml of heptane under stirring at room temperature for 12 hours. The suspension is filtered, the bisulfite complex is washed on the filter with 50 ml of heptane and then suspended in a two-phase mixture made by 100 ml of methylene chloride and 150 ml of a 10% (w/v) aqueous solution of sodium hydroxide. The layers are separated after one hour of stirring at room temperature, the aqueous phase is discarded while the organic layer is washed with water and evaporated under vacuum to give pure ketone.

Example 2

Method for Assaying Activity of Analogs Using Zebrafish Model of Epilepsy

Zebrafish embryos (Danio rerio) heterozygous for the scn1Lab mutation (scn1Lab+/−) are backcrossed with Tupfel longfin wildtype (WT scn1Lab+/+). Adult zebrafish are housed at 28.0° C., on a 14/10 hour light/dark cycle under standard aquaculture conditions. Fertilized eggs are collected via natural spawning. Anaesthetized fish (tricaine 0.02%) are fin-clipped and genotyped by PCR. After genotyping, samples are purified (MinElute PCR Purification Kit) and sequenced by LGC Genomics. Age-matched Tupfel longfin wildtype larvae are used as control group (WT scn1Lab+/+). These embryos and larvae are kept on a 14/10 hour light/dark cycle in embryo medium (Danieaus): 1.5 mM HEPES, pH 7.6, 17.4 mM NaCl, 0.21 mM KCl, 0.12 mM $MgSO_4$, and 0.18 mM $Ca(NO_3)_2$ in an incubator at 28.0° C.

To evaluate the locomotor activity of homozygous scn1Lab−/−mutants and control WT scn1Lab+/+, zebrafish larvae are placed in a 96-well plate in 100 μL of embryo medium from 4 to 8 dpf. Each day the larvae are tracked in an automated tracking device (ZebraBox™ apparatus; Viewpoint, Lyon, France) for 10 min after 30 min habituation (100-second integration interval). All recordings are performed at the same time during daytime period. The total distance in large movements is recorded and quantified using ZebraLab™ software (Viewpoint, Lyon, France). Data are pooled together from at least three independent experiments with at least 24 larvae per condition.

Epileptiform activity is measured by open-field recordings in the zebrafish larval forebrain at 7 dpf. Homozygous scn1Lab−/− mutants and control WT scn1Lab+/+ are embedded in 2% low-melting-point agarose (Invitrogen) to position a glass electrode into the forebrain. This glass electrode is filled with artificial cerebrospinal fluid (aCSF) made from: 124 mM NaCl, 2 mM KCl, 2 mM $MgSO_4$, 2 mM $CaCl_2$, 1.25 mM $KH_2PO_4$, 26 mM $NaHCO_3$ and 10 mM glucose (resistance 1-5 MΩ) and connected to a high-impedance amplifier. Subsequently, recordings are performed in current clamp mode, low-pass filtered at 1 kHz, high-pass filtered 0.1 Hz, digital gain 10, at sampling intervals of 10 μs (MultiClamp 700B amplifier, Digidata 1440A digitizer, both Axon instruments, USA). Single recordings are performed for 10 min. Epileptiform activity is quantified according to the duration of spiking paroxysms as described previously (Orellana-Paucar et al, 2012). Electrograms are analyzed with the aid of Clampfit 10.2 software (Molecular Devices Corporation, USA). Spontaneous epileptiform events are taken into account when the amplitude exceeded three times the background noise and lasted longer than 50 milliseconds (ms). This threshold is chosen due to the less frequent observation of epileptiform events in wildtype ZF larvae with a shorter duration than 50 ms.

Analogs (agonists) and antagonists can be chosen based on their high and selective affinity for the different 5-$HT_{subtype}$ receptors (Ki in nanomolar range), and on their log P value (i.e. >1, expected to exhibit a good bioavailability in zebrafish larvae (Milan, 2003)). Compounds are dissolved in dimethylsulfoxide (DMSO, 99.9% spectroscopy grade, Acros Organics) and diluted in embryo medium to achieve a final DMSO concentration of 0.1% w/v, which also served as a vehicle control (VHC).

To evaluate the maximal tolerated concentration (MTC) of each compound, 6 dpf-old WT scn1Lab+/+ zebrafish larvae are incubated in a 96-well plate (tissue culture plate, flat bottom, FALCON®, USA) with different concentrations of compound or VHC at 28° C. on a 14/10 hour light/dark cycle under standard aquaculture conditions (medium is replenished daily). Each larva is individually checked under the microscope during a period of 48 hours for the following signs of toxicity: decreased or no touch response upon a light touch of the tail, loss of posture, body deformation, edema, changes in heart rate or circulation and death. The maximum tolerated concentration (MTC) is defined as the highest concentration at which no signs of toxicity are observed in 12 out of 12 zebrafish larvae within 48 hours of exposure to sample. The MTC (Tables 1 and 2) is used throughout the work.

Scn1Lab−/− mutants and WT scn1Lab+/+ larvae are arrayed in the same plate and treated at 6 days post fertilization (dpf) with fenfluramine analogs (at their MTC) or VHC in individual wells of a 96-well plate. After incubation at 28° C. on a 14/10 hour light/dark cycle and 30-min chamber habituation 6 and 7 dpf larvae are tracked for locomotor activity for 10 min (100-second integration interval) under dark conditions. An incubation time of 1.5 hours is further referred as short treatment (6 dpf). Furthermore these larvae are analyzed after more than 22 hours incubation (7 dpf), i.e. long treatment. The total locomotor activity is quantified using the parameter lardist and plotted in cm. In some cases, data is pooled together from two (5-$HT_{1B}$-, 5-$HT_{1F}$-, 5-$HT_{T3}$—, 5-$HT_4$-, 5-$HT_{5A}$-, 5-$HT_6$-agonist and all antagonists except 5-$HT_{1B}$- and 5-$HT_7$-antagonists) or three (fenfluramine compounds, 5-$HT_{1A}$-, 5-$HT_{1D}$-, 5-$HT_{1E}$-, 5-$HT_{2A}$-, 5-$HT_{2B}$-, and 5-$HT_{2C}$-agonist) independent experiments with at least 9 larvae per treatment condition.

Epileptiform activity is measured by open-field recordings in the zebrafish larval forebrain at 7 dpf, as described above. Scn1Lab−/− mutants and WT scn1Lab+/+ larvae are incubated with fenfluramine (25 μM), the functional analogs (except for the 5-$HT_{5A}$-agonist) that exhibited locomotor-reducing activity in the previous assay (see below) (MTC), a negative control (3.125 μM 5-HT2B-agonist) or VHC on 6 dpf for a minimum of 22 hours (long treatment). Recordings of 7 dpf larvae, from at least 8 scn1Lab−/−mutant larvae are taken per experimental condition. For treated WT scn1Lab+/+ larvae at least 5 per condition are analyzed, due to the scarce observation of epileptiform activity in wildtype larvae. Electrographic recordings are quantified for the different treatment conditions.

The heads of 7 dpf-old zebrafish larvae are used to determine the amount of the neurotransmitters dopamine, noradrenaline and serotonin present. Six heads per tube are homogenized on ice for one min in 100 µl 0.1 M antioxidant buffer (containing vitamin C). Homogenates are centrifuged at 15 000 g for 15 min at 4° C. Supernatants (70 µl) are transferred to a sterile tube and stored at −80° C. until analysis.

The neurotransmitter determination is based on the microbore LC-ECD method (Sophie Sarre, Katrien Thorré, Ilse Smolders, 1997). The chromatographic system consists of a FAMOS microautosampler of LC Packings/Dionex (Amsterdam, The Netherlands), a 307 piston pump of Gilson (Villiers-le-Bel, France), a DEGASYS DG-1210 degasser of Dionex and a DECADE II electrochemical detector equipped with a µ-VT03 flow cell (0.7 mm glassy carbon working electrode, Ag/AgCl reference electrode, 25 µm spacer) of Antec (Zoeterwoude, The Netherlands). The mobile phase is a mixture of 87% V/V aqueous buffer solution at pH 5.5 (100 mM sodium acetate trihydrate, 20 mM citric acid monohydrate, 2 mM sodium decanesulfonate, 0.5 mM disodium edetate) and 13% V/V acetonitrile. This mobile phase is injected at a flow rate of 60 µL/min. The temperature of the autosampler tray is set on 15° C. and the injection volume is 10 µL. A microbore UniJet C8 column (100×1.0 mm, 5 µm) of Bioanalytical Systems (West Lafayette, Ind., United States) is used as stationary phase. The separation and detection temperature is performed at 35° C., with a detection potential of +450 mV vs Ag/AgCl. Data acquisition is carried out by Clarity chromatography software version 3.0.2 of Data Apex (Prague, The Czech Republic). The amount of neurotransmitter (in nmol) is calculated based on the total mass of six heads.

Statistical analyses are performed using GraphPad Prism 5 software (GraphPad Software, Inc.). The larval locomotor activity is evaluated by using One-way ANOVA, followed by Dunnett's multiple comparison tests. Values are presented as means±standard deviation (SD). LFP measurements (electrographic brain activity) are analyzed by a Mann-Whitney test. Statistically significant differences ($p<0.05$) between a treatment group and the equivalent control groups (scn1Lab−/− mutant or WT scn1Lab+/+) are considered indicative of a decrease or increase in locomotor or electrographic brain activity of zebrafish larvae. The neurotransmitter amount of scn1Lab−/− mutants is compared with WT scn1Lab+/+ larvae by a Student's t-test because all data passed the normality test (D'Agostino & Pearson omnibus normality test).

Example 3

Phenotype-Based Antiepileptic Drug Screening in a Zebrafish Model of Dravet Syndrome Compounds provided by the present disclosure are assessed for their anticonvulsant activity in vitro using a high-throughput mutant zebrafish screening assay. The following methods can be adapted for use in assessing the subject fenfluramine analogs.

Animals: Scn1A

Zebrafish are maintained in a light- and temperature-controlled aquaculture facility under a standard 14:10 h light/dark photoperiod. Adult Heterozygous scn1Lab±mutant zebrafish are housed in 1.5 L tanks at a density of 5-12 fish per tank and fed twice per day (dry flake and/or flake supplemented with live brine shrimp). Water quality is continuously monitored to maintain the following conditions: temperature, 28-30° C.; pH 7.4-8.0; conductivity, 690-710 mS/cm. Zebrafish embryos are maintained in round Petri dishes (catalog # FB0875712, Fisher Scientific) in "embryo medium" consisting of 0.03% Instant Ocean (Aquarium Systems, Inc.) and 000002% methylene blue in reverse osmosis-distilled water.

Larval zebrafish clutches are bred from wild-type (WT; TL strain) or scn1Lab (didys552) heterozygous animals that have been back-crossed to TL wild-type for at least 10 generations. Homozygous mutants (n 6544), which have widely dispersed melanosomes and appear visibly darker as early as 3 d post-fertilization (dpf; FIG. 1b), or WT larvae (n=71) are used in all experiments at 5 or 6 dpf. Embryos and larvae are raised in plastic petri dishes (90 mm diameter, 20 mm depth) and density is limited to 60 per dish. Larvae between 3 and 7 dpf lack discernible sex chromosomes. The care and maintenance protocols comply with requirements [outlined in the Guide for the Care and Use of Animals (ebrary Inc., 2011) and are subject to approval by the Institutional Animal Care and Use Committee (protocol # AN108659-01D)].

Test Agents:

Compounds for screening are provided as 10 mM DMSO solutions. Test agents for locomotion or electrophysiology studies are dissolved in embryo media and are tested at an initial concentration of 100 M, with a final DMSO concentration of 2%. In all drug screen studies, compounds are coded and experiments are performed by investigators who are blind to the nature of the compound. Drug concentrations between 0.5 and 1 mM are used for electrophysiology assays to account for more limited diffusion in agar-embedded larvae.

Seizure Monitoring

Zebrafish larvae are placed individually into 1 well of a clear flat-bottomed 96-well microplate (catalog #260836, Fisher Scientific) containing embryo media. To study changes in locomotion, microplates are placed inside an enclosed motion-tracking device and acclimated to the dark condition for 10-15 min at room temperature. Locomotion plots are obtained for one fish per well at a recording epoch of 10 min using a DanioVision system running EthoVision XT software (DanioVision, Noldus Information Technology); threshold detection settings to identify objects darker than the background are optimized for each experiment. Seizure scoring is performed using the following three-stage scale (Baraban et al., 2005): Stage 0, no or very little swim activity; Stage I, increased, brief bouts of swim activity; Stage II, rapid "whirlpool-like" circling swim behavior; and Stage III, paroxysmal whole-body clonus-like convulsions, and a brief loss of posture. WT fish are normally scored at Stage 0 or I. Plots are analyzed for distance traveled (in millimeters) and mean velocity (in millimeters per second). As reported previously (Winter et al., 2008; Baraban et al., 2013), velocity changes are a more sensitive assay of seizure behavior.

Baseline recordings of seizure behavior are obtained from mutants bathed in embryo media, as described above; a second locomotion plot is then obtained following a solution change to a test compound and an equilibration period of 15-30 min. Criteria for a positive hit designation are as follows: (1) a decrease in mean velocity of 44% (e.g., a value based on the trial-to-trial variability measured in control tracking studies; FIG. 1c); and (2) a reduction to Stage 0 or Stage I seizure behavior in the locomotion plot for at least 50% of the test fish. Each test compound classified as a "positive hit" in the locomotion assay is confirmed, under direct visualization on a stereomicroscope, as the fish being alive based on movement in response to external stimulation and a visible heartbeat following a 60 min drug exposure.

Toxicity (or mortality) is defined as no visible heartbeat or movement in response to external stimulation in at least 50% of the test fish. Hyperexcitability is defined as a compound causing a 44% increase in swim velocity and/or Stage III seizure activity in at least 50% of the test fish. Hits identified in the primary locomotion screen are selected and rescreened, again using the method described above. Select compound stocks that are successful in two primary locomotion assays, and are not classified as toxic in two independent clutches of zebrafish are then subjected to further testing in an electrophysiology assay.

Electrophysiology Assay:

Zebrafish larvae are briefly paralyzed with bungarotoxin (1 mg/ml) and immobilized in 1.2% agarose; field recordings are obtained from forebrain structures. Epileptiform events are identified post hoc in Clampfit (Molecular Devices) and are defined as multi-spike or polyspike upward or downward membrane deflections greater than three times the baseline noise level and 500 ms in duration. During electrophysiology experiments zebrafish larvae are continuously monitored for the presence (or absence) of blood flow and heart beat by direct visualization on an Olympus BX51WI upright microscope equipped with a CCD camera and monitor.

Data Analysis

Data are presented as the mean and SEM, unless stated otherwise. Pairwise statistical significance is determined with a Student's two-tailed unpaired t test, ANOVA, or Mann-Whitney rank sum test, as appropriate, unless stated otherwise. Results are considered significant at p 0.05, unless otherwise indicated.

Example 4

Multi-Electrode Array Screening for Anticonvulsant Activity

Test agents are assessed as therapeutic targets by measuring their effects on electrophysiological parameters identified as reflecting disease using multi-electrode arrays recording (MEAs) across principal regions of hippocampal brain slices (CA1, CA3, dentate gyrus) taken from untreated wild type and DS KO mice.

Tissue Preparation:

Male and female 129S wild-type and DS KO mice, are humanely killed by cervical dislocation. No more than one slice per animal is used to investigate any one experimental condition. Brains are swiftly (<2 min) removed and placed in chilled, carboxygenated (95% $O_2$:5% $CO_2$) artificial cerebrospinal fluid (aCSF), comprising (mM) NaCl 124, KCl3, $KH_2PO_4$ 1.25, $NaHCO_3$ 36, $MgSO_4.6H_2O$ 1, d-glucose 10 and $CaCl_2$ 2. Conventional transverse hippocampal slices (Egert et al., 2002a) are cut at a thickness of 450 m using a Campden Vibroslice/M tissue slicer (Campden Instruments, Loughborough, UK) and left to rest for at least 1 h in aCSF at room temperature before recording commenced.

For $Mg^{2+}$-free induction of epileptiform activity, $MgSO_4.6H_2O$ is omitted without substitution from the aCSF. Standard or $Mg^{2+}$-free aCSF is used throughout dissection and recording as appropriate with positive controls, test agents and vehicle added during recording from previously prepared aliquots of concentrated stocks. Aliquots are frozen immediately after preparation and individually thawed before use. All reagents and drugs are obtained from Sigma-Aldrich (Poole, UK). Positive controls and test agents are dissolved in DMSO at 1000× working concentration and stored at −20° C. until use before incorporation into aCSF; maximum DMSO bath concentration is 0.1% 2.2.

Mea Recordings:

Electrical activity across each hippocampal slice is monitored and recorded using MEAs (59 electrodes each 30μ diameter with 200 μm spacing and 100 μm recording radius, FIG. 1A; Multi Channel Systems, GmbH, Reutlingen, Germany).

Prior to recording, MEAs are cleaned with 5% (w/v) Terg-A-Zyme (Cole-Palmer, London, UK), methanol and finally distilled water.

Slices are adhered to MEAs using an applied (~41) and evaporated cellulose nitrate solution in methanol (0.24%, w/v, Protran Nitrocellulose Transfer Membranes; Schleicher & Schuell Bioscience Inc., NH, USA; Ma et al., 2008). Slice position on the MEA is ascertained by observation on a Nikon TS-51 microscope (Nikon, Japan) at magnification ×4, with images of the slice and electrode positions being acquired via a Mikro-Okular camera (Meade Instruments Corp., CA, USA; FIG. 1A) to a PC. Once attached, slices are continually perfused with carboxygenated aCSF (~2 ml/min). Slices are maintained at 21° C. in order to provide good separation of synaptically mediated LFP components and maximize slice viability time. Slice viability and contact with MEA electrodes are assessed by applying voltage pulses (STG2004 stimulator, Multi Channel Systems GmbH, Reutlingen, Germany) through MEA electrodes on the slice (200 s biphasic pulses, ±0.5-3.0 V) to evoke local field potentials.

For each agent, 12-15 recordings are made per condition and in each tissue type (mutant and wildtype). Signals are amplified (1200× gain), by a 120-channel dual headstage amplifier (MEA60 System, Multi Channel Systems GmbH, Reutlingen, Germany) and simultaneously sampled at a minimum of 10 kHz per channel on all 60 channels. Data acquisition is to a PC using MC Rack software (Multi Channel Systems GmbH, Reutlingen, Germany) to monitor and record data for offline analysis.

Data Analysis:

Data analyses are performed using in-house scripts for Matlab 6.5 and 7.0.4 (Mathworks, Natick, Mass., USA; Matlab scripts used throughout this study available on request from authors). Microsoft Excel (Microsoft, Redmond, USA) and MC DataTool (Multi Channel Systems GmbH, Reutlingen, Germany) are also used to process and present data.

Raw data are filtered using a 2 Hz high pass 2nd order Butterworth filter to remove very low frequency artefacts associated with bath perfusion. Changes in burst amplitude and frequency during control experiments are assessed using in-house Matlab 7.0.4 scripts. Data are downsampled from 10 kHz to 500 Hz, whereupon a single Matlab script returned the peak amplitude (V) of each burst within an experiment and the time at which the peaks occurred (s). These data are used for representative plots of amplitude and frequency.

Additionally, mean amplitudes are calculated at 10 min intervals using the peak amplitudes of the ten bursts directly preceding the time of interest. The same ten bursts are also used to calculate frequency where: frequency=10/(time of last burst−time of first burst). When data of this type from different electrodes and slices are pooled, the first burst from each electrode recording is considered to have occurred at 0 s; subsequent bursts are offset by the same amount. This improved comparability between recordings from different sources. In control experiments assessing amplitude and frequency changes, mean amplitude and frequency values are normalized to the value calculated at 30 min after bursting commenced.

Burst propagation paths are determined by constructing contour plots from raw data files at one frame per sampling point (10 kHz) using an in-house adaptation of MEATools (Egert et al., 2002b) in Matlab 6.5 and interpolated using a 5 point Savitzky-Golay filter before export to JPEG image format. Individual JPEGs are concatenated and converted into AVI animations using Photolapse (http://home.hc-cnet.nl/s.vd.palen/photolapsedlc.html) for later low speed replay. After determining burst initiation site, termination site and resulting propagation path, the time that burst peaks occurred at electrode positions closest to burst initiation (CA3) and termination (CA1) sites are ascertained in MC Rack. Initiation to termination distances is calculated using ImageJ (Abramoff et al., 2004) and propagation speed thusly derived from time and distance values. Mean propagation speeds are derived from pooled data.

Spectrograms are produced with Neuroexplorer 4.045 (NexTechnologies, Littleton, Mass., USA) using 20 ms window shifts, 8192 fast Fourier transform (FFT) frequency divisions and a frequency cut-off at 250 Hz. Spectrograms are normalized for comparison by expression of spectral power as the log of the power spectral density (dB). Power spectral density values are produced using Neuroexplorer using 2048 FFT frequency divisions with a frequency cut-off of 250 Hz. Representative power spectral density plots are shown for the frequency range 0-50 Hz and are smoothed using a five point Gaussian filter. However, the full unsmoothed frequency range (0-250 Hz) is used for quantification of total power changes in the absence and presence of anticonvulsant drugs. Data sets of equal duration (≥150 s) in epileptiform and anticonvulsant treated states are used in the construction of power spectra and subsequent quantification.

Changes in total power in the presence of anticonvulsant drugs are expressed as a percentage of the total power in the presence of 100M4-AP or absence of Mg2+ for each electrode. Percentage values from individual electrodes are then pooled as hippocampal regions (CA1, CA3 and dentate gyrus (DG)) before averaging. Data from ≥4 electrodes from >1 slice preparations are analyzed for each region. In experiments where anticonvulsants are added, bursting is first induced by application of 100M 4-AP or Mg2+-free aCSF; 30 min after bursting commenced, phenobarbital or felbamate are applied. Differences in burst frequency, amplitude and duration are thus assessed between the 10 bursts prior to drug application (at 30 min after bursting commenced), and the 10 bursts 30 min after drugs had been applied. If no bursts are recorded in the last 5 min of the 30 min after AED application, bursting is considered to have been abolished. In this instance, continuing slice viability and fidelity of contact with the MEA are confirmed by evocation of field potentials via electrode stimulation as described above.

Statistical significance is determined by non-parametric Mann-Whitney U-test in the case of all normalised data and comparisons of frequency and latency between models. The significance of anticonvulsant drug effects on propagation speeds is tested using a two-tailed paired Students t-test. $p \leq 0.05$ is considered significant in all cases. All data are presented as means±S.E.M and data is given for each hippocampal region (DG, CA3, CA1).

Example 5

Survival Studies

Dose-response curves are generated for candidate therapeutic agents using wild-type and $Scn1a^{-/-}$ mutant knockout mice.

Treatment of Animals:

129S wild-type mice (controls) and 129S Scn1a knock-out mice ("DS KO mice") are obtained from The Jackson Laboratory (MMRRC Stock No: 37107-JAX). All animal procedures comply with all applicable animal welfare regulations.

Groups of 10-12 animals having roughly equal numbers of male and females are treated with either vehicle, a positive control, or a test agent. Animals are injected subcutaneously with 0.08 ml injection volume twice daily at 0900 and 1600 hours from P8 until sacrifice. Injection sites are rotated in the following order: left shoulder, right shoulder, left hip, right hip. Dose concentrations are adjusted to retain consistent volumes of administration.

Following treatment, animals are sacrificed at 2 days post-weaning (P23/24) or sooner as required by mathematical model. Animals are then assessed using Kolmogorov-Smirnov welfare scoring (compared between groups (Massey, F. J. "The Kolmogorov-Smirnov Test for Goodness of Fit." Journal of the American Statistical Association. Vol. 46, No. 253, 1951, pp. 68-78) and Mantel-Cox or Gehan-Breslow-Wilcoxon mortality tests (for the former, see Mantel N., "Evaluation of survival data and two new rank order statistics arising in its consideration" Cancer Chemother Rep. 1966 PMID: 5910392). Data obtained is subjected to statistical analysis (see below) and is presented as median, IQR and max/min (except % mortality).

Example 6

Assessment of Compounds as Potential Therapeutic Agents for Dravet Syndrome Patients Using Induced Pluripotent Stem Cell Cortical Neurons The therapeutic efficacy of compounds of interest, alone and in combination with other commonly used anti-convulsants, is assessed using induced pluripotent stem cell (iPSC) cortical neurons derived from Dravet syndrome patients who are known responders to fenfluramine Results obtained for test agents are compared to those obtained for fenfluramine. The following methods can be adapted for use in assessing the subject fenefluramine analogs.

A. Materials and Methods

Differentiation of Human iPSCs into Cortical Neurons iPSC cells taken from Dravet syndrome patients known to respond to fenfluramine are differentiated into cortical pyramid-like neurons and cortical interneurons.

Generation of Cortical Pyramidal-Like Neurons iPSCs are first dissociated into single cells with Accutase or 0.5 mM EDTA (Lonza), and plated onto gelatin-coated dishes for 1 h in hESC medium with 10 μM ROCK inhibitor. Suspended iPSCs are then re-plated on Matrigel-coated 12-well plates in MEFconditioned hESC medium with 10 ng/ml FGF2. At 95% confluence, the medium is changed to 3N medium supplemented with 1 μM Dorsomorphin and 10

μM SB431542. Cells are cultured for 8-11 d, and neural induction is monitored by the appearance of "neural rosettes". Neuroepithelial cells are dissociated with Dispase or 5 mM EDTA and replated in 3N medium with 20 ng/ml FGF2 on Matrigelcoated plates. After 2-4 d, FGF2 is withdrawn to promote differentiation. Cultures are passaged with Accutase, replated at $5\times10^5$ on 60 mm Matrigel-coated plates seeded with rodent forebrain glia or human iPS derived glia cells in 3N medium and maintained for up to 100 d with medium changes every other day.

Generation of Cortical Interneurons iPSC embryoid bodies (EBs) are plated in a neural induction medium similar to that described above with TGF-β inhibitors until a neuroepithelial sheet forms. The neuroepithelial sheet are then patterned to medial ganglion eminence (MGE)-like progenitors using high concentrations of Pur and differentiate the MGE-like progenitors to GABAergic interneurons. A nearly pure population (90%) of GABAergic interneurons is generated, and confirmed after 7 weeks in culture by performing immunocytochemistry for GABA.

Measurement of Voltage-Gated Sodium Current and Action Potential Firing in Whole Cells The effects of compounds of interest, alone and in the presence of known AEDs, on voltage-gated sodium current and action potential firing in whole cell is measured using whole cell voltage and current clamp recordings. As a first step, the effect of increasing concentrations of test compounds on sodium current is measured under voltage-clamp. The effect of test compounds on evoked and spontaneous action potential firing is then measured under current clamp.

Perfusion of Drugs During Voltage- or Current-Clamp Experiments

Test compounds (at final concentrations of 10 μM to 1 mM) or vehicle (either sodium current recording solution or ACSF) are perfused onto neurons following recordings of basal sodium current levels or action potential firing. Effects of acute and long-term drug applications are then measured.

Changes in voltage-sensitive sodium current and action potential firing can be assessed in response to increasing concentrations of a compound of interest, in the presence and absence of the following AEDs frequently prescribed for Dravet Syndrome, at the final concentration indicated: topiramate (200 μM), stiripentol (100 μM), valproic acid (250 μM), and clobazam (3 μM).

Voltage-Clamp Recordings

Voltage-clamp recordings are performed as previously described. See Brackenbury et. al, Abnormal neuronal patterning occurs during early postnatal brain development of Scn1b-null mice and precedes hyperexcitability. Proc Natl Acad Sci USA. 2013; 110(3):1089-94. PMCID: 3549092.

Isolated sodium currents are recorded from single neurons (bipolar or pyramidal) at RT (21-22° C.) in the presence of a bath solution that contains (in mM): 120 NaCl, 1 BaCl2, 2 MgCl2, 0.2 CdCl2, 1 CaCl, 10 HEPES, 20 TEA-Cl and 10 glucose (pH 7.35 with CsOH, Osmolarity: 300-305 mOsM). Fire-polished patch pipettes are generated from borosilicate glass capillaries (Warner Instrument Corp.) using a Sutter P-97 puller (Sutter Instrument Co.) and are filled with an internal solution containing (in mM): 1 NaCl, 177 N-methyl-D-glucamine, 10 EGTA, 2 MgCl2, 40 HEPES, and 25 phosphocreatine-tris (pH 7.2 with H2SO4). Recordings are performed within 10-120 min after the culture medium is replaced by bath recording solution and the dish with cells is placed on the recording setup. Experimental data collected includes current-voltage relationships, current density, voltage-dependence of activation, voltage-dependence of inactivation, and recovery from inactivation.

Current Clamp Recordings

Current clamp recordings are performed as described in Liu et. al, Dravet syndrome patient-derived neurons suggest a novel epilepsy mechanism. Ann Neurol. 2013; 74(1):128-39. PMCID: 3775921

For current-clamp recordings of action potentials in iPSC-derived neurons, the patch pipette is filled with internal solution consisting of (in mM): 135, K-gluconate; 4, NaCl; 0.5, CaCl4; 10, HEPES; 5, EGTA, 2, Mg-ATP and 0.4, GTP (pH 7.3, adjusted with KOH). iPSC neurons are bathed in a solution consisting of (in mM): 115, NaCl; 2.5, KCl; 1, MgCl2; 1.25, KH2PO4; 26, NaHCO3; 2, CaCl; 10 HEPES and 10, D-glucose (pH 7.4, adjusted with NaOH). Individual action potentials are evoked from their resting membrane potential by injection of a series of 1 ms depolarizing currents beginning from the subthreshold level until consistent generation of action potentials at 0.02 nA-increment. The minimal current required for initiation of the first action potential is defined as the threshold current. Repetitive spike firing is evoked by injection of a 1500 ms depolarizing current (0.02 nA) from a holding potential at their resting levels. Spontaneous firing is recorded from neurons held at their resting membrane potential.

Quantitative data are presented as mean and SEM. Pairwise statistical significance are determined with Student's two-tailed paired/unpaired t-tests, or Mann-Whitney Rank Sum tests, as appropriate. Multiple comparisons are made using ANOVA followed by Tukey post-hoc analysis. Results are considered significant at $P<0.05$.

Measurement of Spontaneous Action Potential Firing of iPSC Cortical Neuron Clusters Administration of Drugs During MEA Recordings:

Increasing concentrations of test compounds and vehicle are added to the media of each well of a 96-well plate (6 wells per subject per condition, with one control and one Dravet subject per plate) containing human iPSC neurons following recordings of basal activity levels. Each well contains 8 electrodes for extracellular recordings of spontaneous action potentials. Recordings are made for 5 minutes every 15 minutes over a 1-hour period, and are repeated every week over a 3 week period during weeks 5-7 of neuronal differentiation. All experiments are performed in duplicate.

MEA Recordings

Control and Dravet Syndrome human iPSC-derived neurons are cultured on the Axion 96-well MEA chips, which contain 8 electrodes per well. Plates are coated with fibronectin and seeded with neural progenitors at the density of $1.3\times10^6$ cells/ml. The extracellular electrical signals detected by the MEA system are amplified using the built-in Axion amplifier and sampling software, and the closed system maintains the cells at 37 degrees C. and allows for maintaining a 5% CO2 environment for prolonged recordings. Action potential analyses are performed using NeuroExplorer software. Spike rates per well and per electrode, bursting rates, degree of synchronous discharges (i.e., occurring simultaneously at multiple electrodes) and local field potential morphology are determined.

Notwithstanding the appended claims, the disclosure set forth herein is also defined by the following clauses:

Clause 1. A method of treating epilepsy or a neurological related disease, comprising administering to a patient in need thereof a therapeutically effective amount of a compound of formula (I):

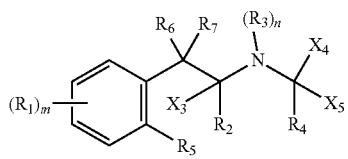

(I)

wherein:

$R_1$, $R_2$, $R_3$, $R_4$, $R_5$, $R_6$ and $R_7$ are independently selected from hydrogen, halogen, $X_1$, $X_2$, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl, substituted heterocycle, or together with a second $R^1$-$R^7$ group form a cycloalkyl ring, a heterocycle ring, an aryl ring or a heteroaryl ring that is optionally substituted wherein $R_2$ and $R_5$, $R_2$ and $R_4$, $R_1$ and $R_5$, $R_6$ and $R_7$, and/or $R_3$ and $R_6$ are cyclically linked;

$X_1$-$X_5$ are each independently H, D, F, alkyl or substituted alkyl;

m is 0-4; and n is 1 or 2, wherein when n is 2 the nitrogen is positively charged;

or a pharmaceutically acceptable salt thereof.

Clause 2. The method of clause 1, wherein the compound is a compound having the formula (II):

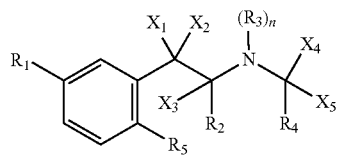

(II)

wherein:

$R_1$ is an alkyl, a substituted alkyl (e.g., $CF_3$) or $SF_5$;

$R_2$, $R_3$, $R_4$ and $R_5$ are independently selected from hydrogen, halogen, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl and substituted heterocycle, where $R_2$ and $R_5$ or $R_2$ and $R_4$ are optionally cyclically linked;

$X_1$-$X_5$ are each independently H, D, F, alkyl or substituted alkyl; and n is 1 or 2, wherein when n is 2 the nitrogen is positively charged;

or a salt thereof.

Clause 3. The method of clause 1 or 2, wherein the compound is a compound having the formula (III):

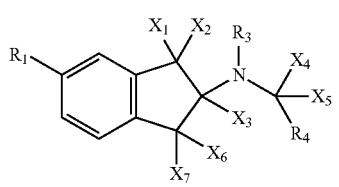

(III)

wherein $X_1$-$X_7$ are each independently H, D or F, and $R_1$, $R_3$ and $R_4$ are as defined in any of the embodiments of formula (I).

Clause 4. The method of clause 1 or 2, wherein the compound is a compound having the formula (IV):

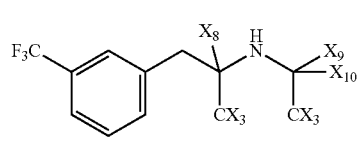

(IV)

wherein $X_8$-$X_{10}$ and each X are independently H, D or F, provided at least one $X_8$-$X_{10}$ or X is F.

Clause 5. The method of clause 4, wherein the compound is a compound having one of the following structures:

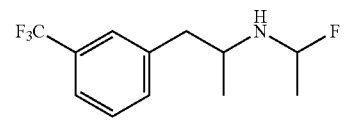

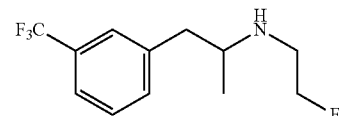

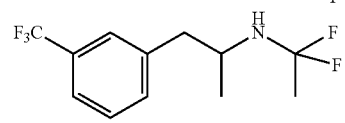

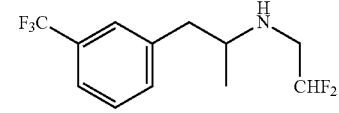

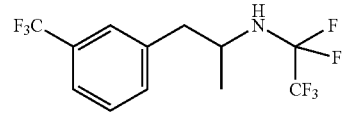

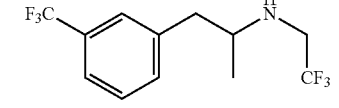

Clause 6. The method of any one of clauses 1, 2 and 4, wherein the compound is a compound having one of the formulae (IVa)-(IVc):

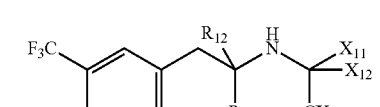

(IVa)

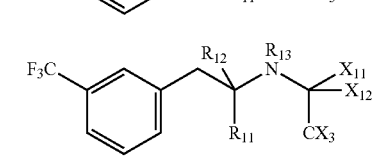

(IVb)

-continued

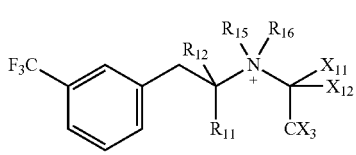
(IVc)

wherein $X_{11}$, $X_{12}$ and each X is independently H, D or F; and
$R_{11}$-$R_{16}$ are each independently an alkyl or a substituted alkyl.

Clause 7. The method of clause 1, wherein the compound is a compound having the formula (V):

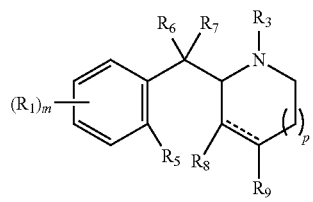
(V)

wherein $R_1$, $R_3$, $R_5$, $R_6$, $R_7$ and m are as defined above, p is 0, 1 or 2, and $R_8$ and $R_9$ are independently selected from hydrogen, halogen, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl and substituted heterocycle, or $R_8$ and $R_9$ are cyclically linked to form a 5 or 6-membered cycloalkyl, heterocycle, aryl or heteroaryl ring, that is optionally further substituted, where the dashed bond represents a single or double covalent bond.

Clause 8. The method of clause 7, wherein the compound is a compound having the formula (VI):

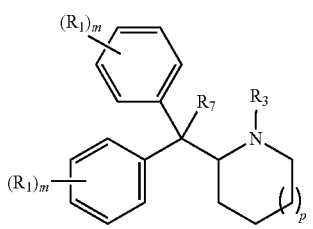
(VI)

wherein $R_1$, $R_3$, $R_7$, and m are as defined above, and p is 0, 1 or 2.

Clause 9. The method of clause 8, wherein the compound is a compound having one of the following structures:

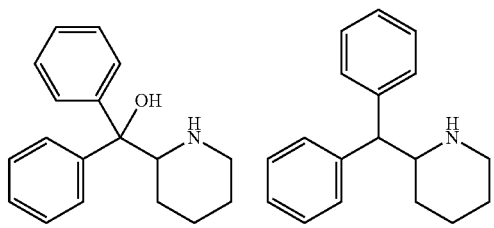

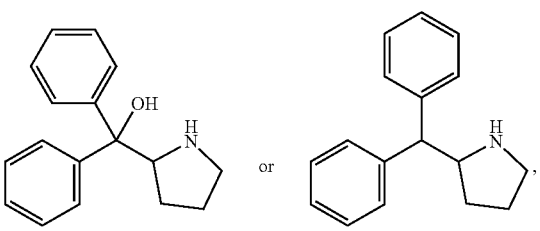

or a prodrug thereof, or a stereoisomer thereof, or a salt thereof.

Clause 10. The method of clause 7, wherein the compound is a compound having formula (VII):

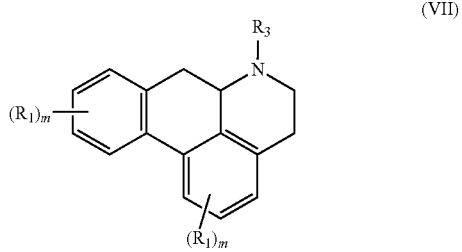
(VII)

or a prodrug thereof, or a stereoisomer thereof, or a salt thereof.

Clause 11. The method of clause 10, wherein the compound has the structure:

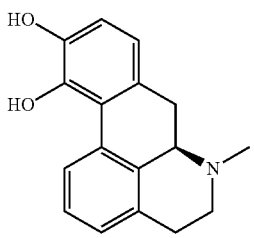 [SMILES: CN1CCc2cccc3c2[C@H]1Cc1ccc(O)c(O)c1-3]

or a prodrug thereof, or a stereoisomer thereof, or a salt thereof.

Clause 12. The method of clause 1, wherein the compound is a compound having the formula (VIII):

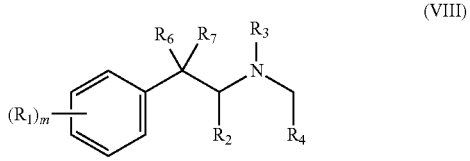
(VIII)

wherein $R_1$-$R_4$, $R_6$, $R_7$ and m are as defined above.

Clause 13. The method of clause 12, wherein the compound is a compound having the formula (IX):

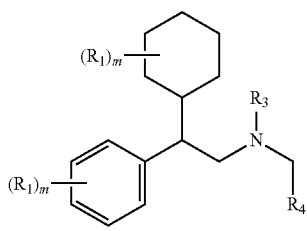

wherein R₁, R₃, R₄, and each m are as defined above.

Clause 14. The method of clause 13, wherein the compound has the structure:

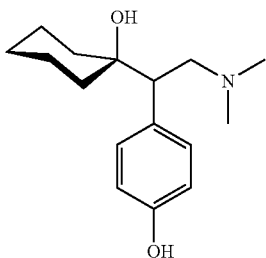

or a prodrug thereof, or a stereoisomer thereof, or a salt thereof.

Clause 15. The method of clause 12, wherein the compound is a compound having the formula (X):

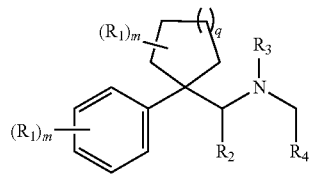

wherein R₁-R₄, and each m are as defined above, and q is 0, 1 or 2.

Clause 16. The method of clause 15, wherein the compound is a compound having has the formula (XIa) or (XIb):

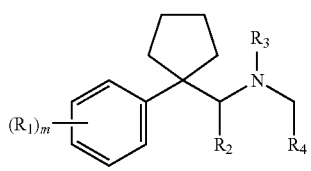

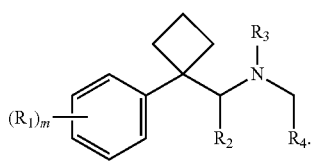

Clause 17. The method of clause 16, wherein the compound has the structure:

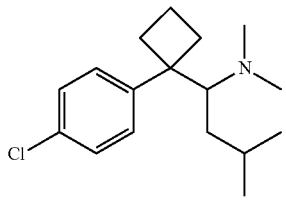 [SMILES: CC(C)CC(N(C)C)C1(c2ccc(Cl)cc2)CCC1]

or a prodrug thereof, or a stereoisomer thereof, or a salt thereof.

Clause 18. The method of clause 7, further comprising co-administering to the subject an antiepileptic agent.

Clause 19. A method of suppressing appetite in a subject, comprising administering to the subject in need thereof an appetite suppressing-amount of a compound of formula (I):

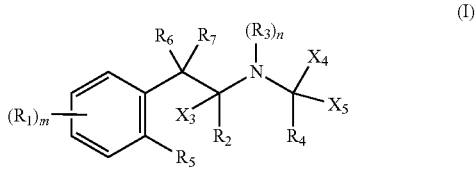

wherein:
R₁, R₂, R₃, R₄, R₅, R₆ and R₇ are independently selected from hydrogen, halogen, X₁, X₂, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl, substituted heterocycle, or together with a second R¹-R⁷ group form a cycloalkyl ring, a heterocycle ring, an aryl ring or a heteroaryl ring that is optionally substituted wherein R₂ and R₅, R₂ and R₄, R₁ and R₅, R₆ and R₇, and/or R₃ and R₆ are cyclically linked;
X₁-X₅ are each independently H, D, F, alkyl or substituted alkyl;
m is 0-4; and
n is 1 or 2, wherein when n is 2 the nitrogen is positively charged;
or a pharmaceutically acceptable salt thereof.

Clause 20. The method of clause 19, wherein the compound is a compound having the formula (II):

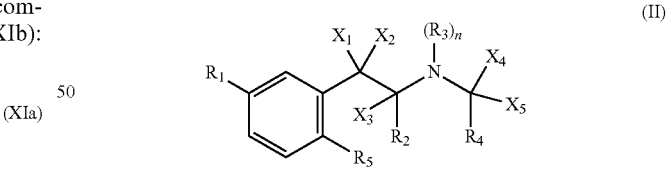

wherein:
R₁ is an alkyl, a substituted alkyl (e.g., CF₃) or SF₅;
R₂, R₃, R₄ and R₅ are independently selected from hydrogen, halogen, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl and substituted heterocycle, where R₂ and R₅ or R₂ and R₄ are optionally cyclically linked;
X₁-X₅ are each independently H, D, F, alkyl or substituted alkyl; and
n is 1 or 2, wherein when n is 2 the nitrogen is positively charged;
or a salt thereof.

Clause 21. The method of clause 19 or 20, wherein the compound is a compound having the formula (III):

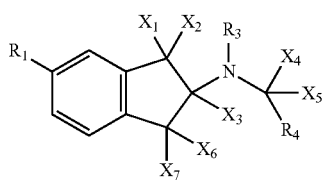

wherein $X_1$-$X_7$ are each independently H, D or F, and $R_1$, $R_3$ and $R_4$ are as defined in any of the embodiments of formula (I).

Clause 22. The method of clause 19 or 20, wherein the compound is a compound having the formula (IV):

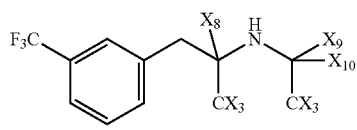

wherein $X_8$-$X_{10}$ and each X are independently H, D or F, provided at least one $X_8$-$X_{10}$ or X is F.

Clause 23. The method of clause 22, wherein the compound is a compound having one of the following structures:

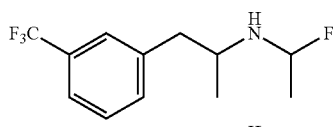

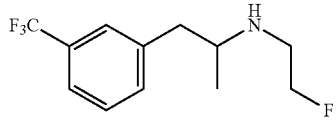

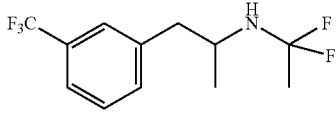

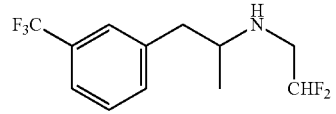

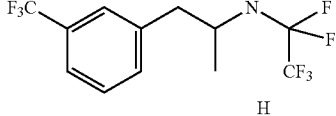

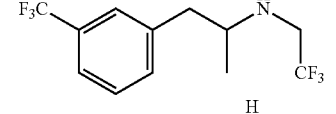

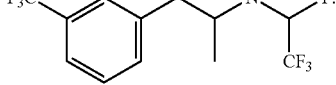

Clause 24. The method of any one of clauses 19, 20 and 22, wherein the compound is a compound having one of the formulae (IVa)-(IVc):

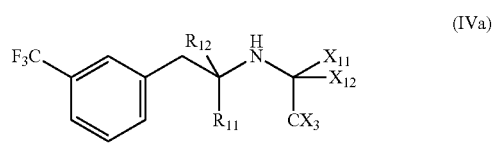

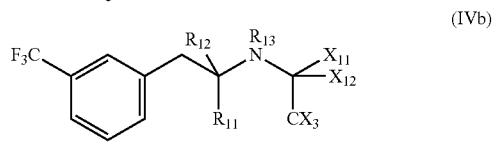

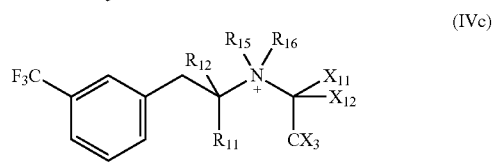

wherein $X_{11}$, $X_{12}$ and each X is independently H, D or F; and $R_{11}$-$R_{16}$ are each independently an alkyl or a substituted alkyl.

Clause 25. The method of clause 19, wherein the compound is a compound having the formula (V):

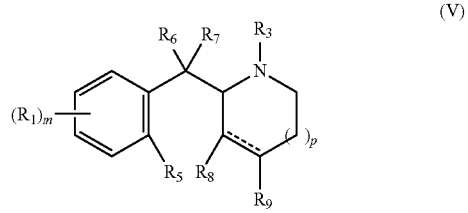

wherein $R_1$, $R_3$, $R_5$, $R_6$, $R_7$ and m are as defined above, p is 0, 1 or 2, and $R_8$ and $R_9$ are independently selected from hydrogen, halogen, alkoxy, acyl, substituted acyl, carboxy, cyano, hydroxy, alkoxy, substituted alkoxy, alkyl, substituted alkyl, aryl, substituted aryl, heterocycle, heteroaryl, substituted heteroaryl and substituted heterocycle, or $R_8$ and $R_9$ are cyclically linked to form a 5 or 6-membered cycloalkyl, heterocycle, aryl or heteroaryl ring, that is optionally further substituted, where the dashed bond represents a single or double covalent bond.

Clause 26. The method of clause 25, wherein the compound is a compound having the formula (VI):

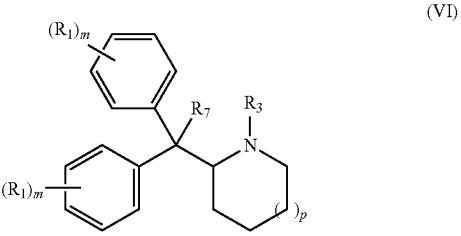

wherein $R_1$, $R_3$, $R_7$, and m are as defined above, and p is 0, 1 or 2.

Clause 27. The method of clause 25, wherein the compound is a compound having one of the following structures:

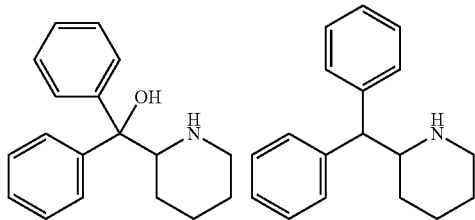

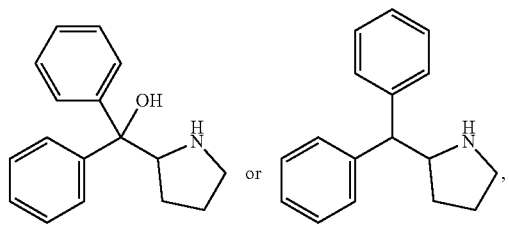

or a prodrug thereof, or a stereoisomer thereof, or a salt thereof.

Clause 28. The method of clause 27, wherein the compound is a compound having formula (VII):

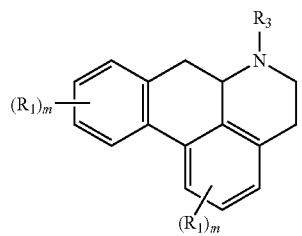

(VII)

or a prodrug thereof, or a stereoisomer thereof, or a salt thereof.

Clause 29. The method of clause 28, wherein the compound has the structure:

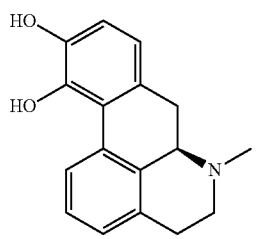 [SMILES: CN1CCc2cccc3c2[C@H]1Cc1ccc(O)c(O)c1-3]

or a prodrug thereof, or a stereoisomer thereof, or a salt thereof.

Clause 30. The method of clause 19, wherein the compound is a compound having the formula (VIII):

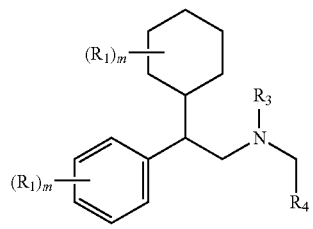

(VIII)

wherein $R_1$-$R_4$, $R_6$, $R_7$ and m are as defined above.

Clause 31. The method of clause 30, wherein the compound is a compound having the formula (IX):

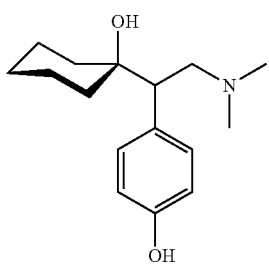

(IX)

wherein $R_1$, $R_3$, $R_4$, and each m are as defined above.

Clause 32. The method of clause 31, wherein the compound has the structure:

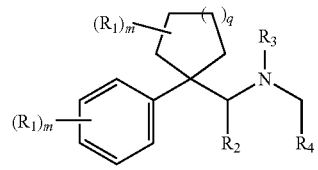

or a prodrug thereof, or a stereoisomer thereof, or a salt thereof.

Clause 33. The method of clause 30, wherein the compound is a compound having the formula (X):

(X)

wherein $R_1$-$R_4$, and each m are as defined above, and q is 0, 1 or 2.

Clause 34. The method of clause 33, wherein the compound is a compound having has the formula (XIa) or (XIb):

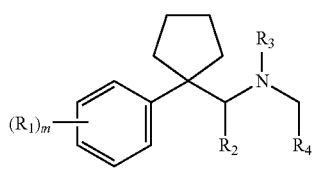

(XIa)

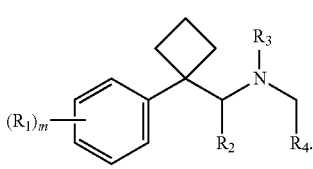

(XIb)

Clause 35. The method of clause 34, wherein the compound has the structure:

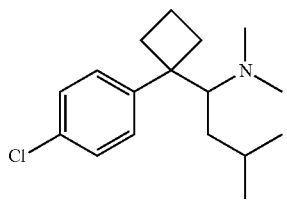 [SMILES: CC(C)CC(N(C)C)C1(c2ccc(Cl)cc2)CCC1]

or a prodrug thereof, or a stereoisomer thereof, or a salt thereof.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of treating epilepsy comprising:
administering to a patient in need thereof a therapeutically effective amount of a metabolism-resistant fenfluramine analog having a structure selected from the group consisting of:

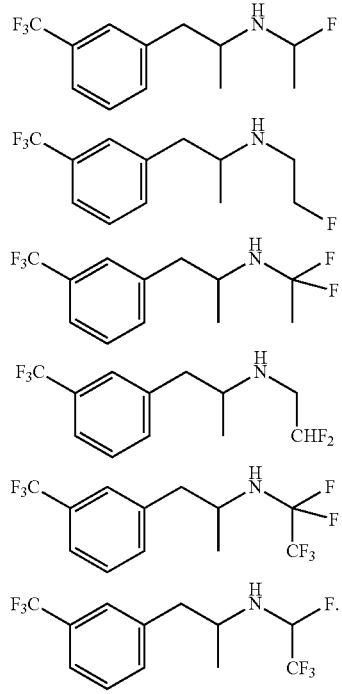

2. The method of claim 1, wherein the compound is

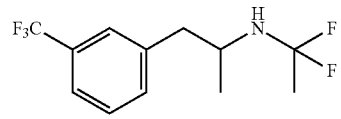 [SMILES: CC(Cc1cccc(C(F)(F)F)c1)NC(C)(F)F]

which is (1,1-difluoroethyl)({1-[3-(trifluoromethyl)phenyl]propan-2-yl})amine.

3. The method of claim 1, wherein the method further comprises co-administering to the patient an antiepileptic agent.

* * * * *